United States Patent

Green et al.

[11] Patent Number: 5,847,291
[45] Date of Patent: Dec. 8, 1998

[54] AIR SAMPLER WITH TRAP

[75] Inventors: Thomas B. Green, Batavia; Larry J. DaPrato, Cincinnati; Michael A. Hill, Loveland; Valerie J. Naughton, Maineville; Edmund T. Lewis, West Chester, all of Ohio; Todd A. Wolsing, Taylor Mill, Ky.; Joseph A. Borer, Cincinnati, Ohio

[73] Assignee: Tekmar Company, Cincinnati, Ohio

[21] Appl. No.: 803,018

[22] Filed: Feb. 21, 1997

Related U.S. Application Data

[63] Continuation of Ser. No. 556,620, Nov. 13, 1995, abandoned.

[51] Int. Cl.[6] .................................................. G01N 1/00
[52] U.S. Cl. .............................................................. 73/863.33
[58] Field of Search ........................... 73/863.01, 863.11, 73/863.12, 863.21, 863.31, 863.33, 863.83, 864.81–864.83, 864.87, 864.21

[56] References Cited

U.S. PATENT DOCUMENTS

| | | | |
|---|---|---|---|
| 3,653,840 | 4/1972 | Silas | 73/23.42 |
| 3,860,393 | 1/1975 | Campen, Jr. | |
| 3,976,450 | 8/1976 | Marcote et al. | 55/158 |
| 4,046,014 | 9/1977 | Boehringer et al. | 73/421.5 R |
| 4,237,733 | 12/1980 | Kolb et al. | 73/864.21 |
| 4,610,169 | 9/1986 | Clavell, Jr. | 73/863.12 |
| 4,702,115 | 10/1987 | Brabandt et al. | 73/864.85 |
| 4,704,910 | 11/1987 | Conrad | 73/863.21 |
| 5,321,984 | 6/1994 | Stroupe | 73/863.11 |
| 5,349,833 | 9/1994 | Pardee et al. | 62/55.5 |
| 5,384,095 | 1/1995 | Golz et al. | 422/100 |
| 5,563,352 | 10/1996 | Helmig | 73/863.12 |

OTHER PUBLICATIONS

"Entech 7000—Automated Programmable Preconcentrator", Entech Instruments, Inc.
Brochure: "SUPELCO Chromatography Products", Supelco, Inc., pp. 377–388, 1994.
TEKMAR ALS 2016/ALS 2032—User Manual, Jan. 31, 1994.

*Primary Examiner*—Robert Raevis
*Attorney, Agent, or Firm*—Westman, Champlin & Kelly, P.A.

[57] ABSTRACT

An air sampler includes a stand adapted to support sample enclosures at spaced-apart locations. A multiposition valve is mounted to the stand. The multiposition valve has a plurality of inlet ports and an outlet port selectively fluidly coupled to any of the plurality of inlet ports. A plurality of inlet lines connects the sample enclosures to the inlet ports. A concentrator trap mounted on the stand and coupled to the outlet port concentrates selected constituents from one of the sample enclosures.

13 Claims, 23 Drawing Sheets

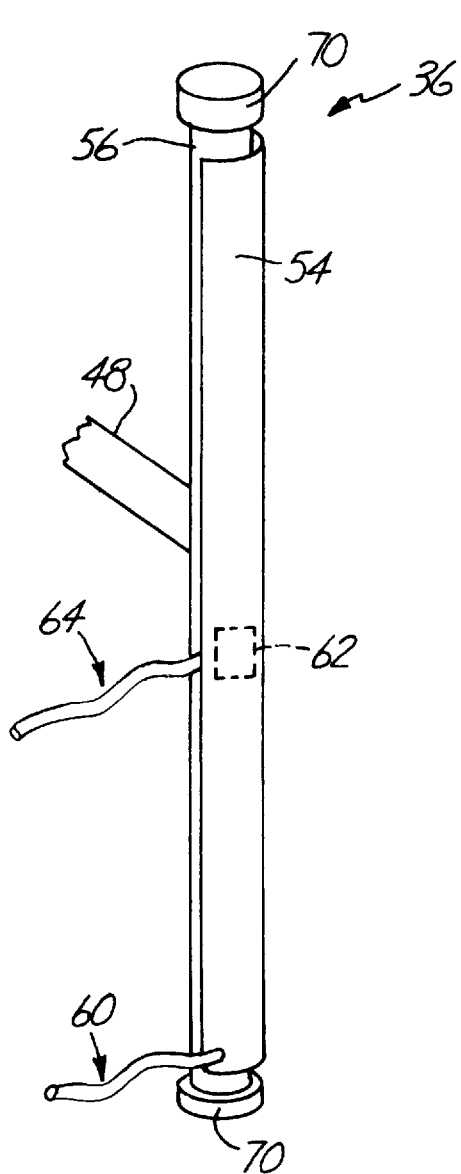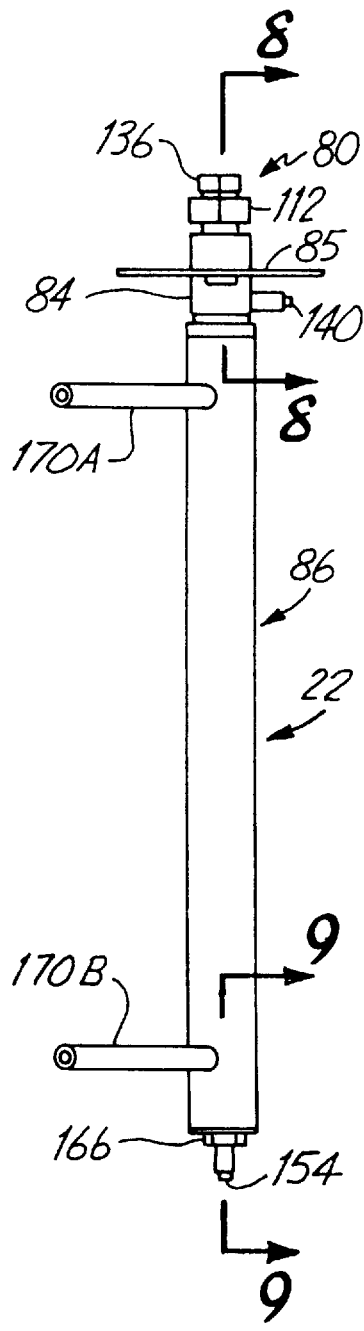
Fig. 6
Fig. 7

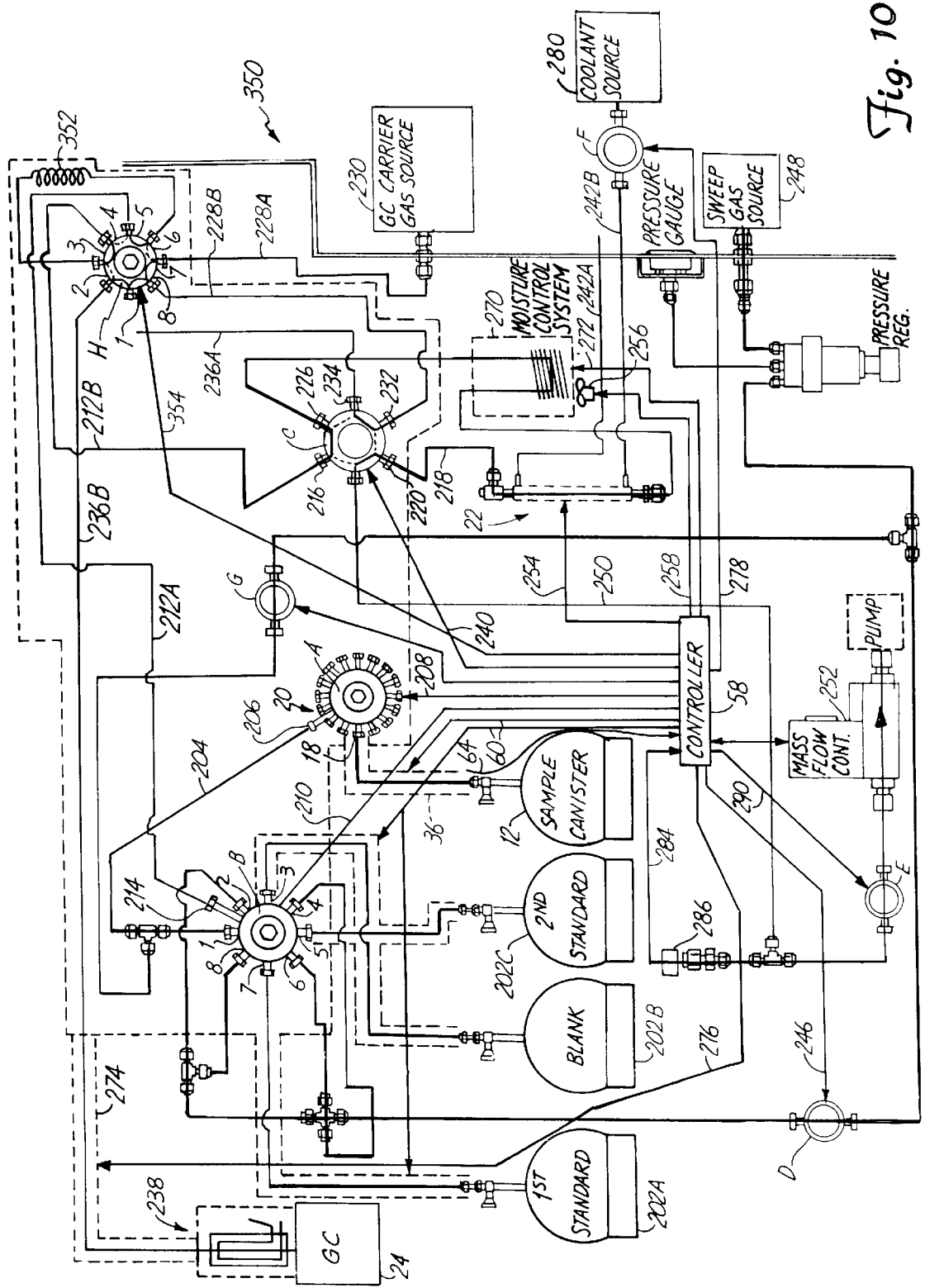

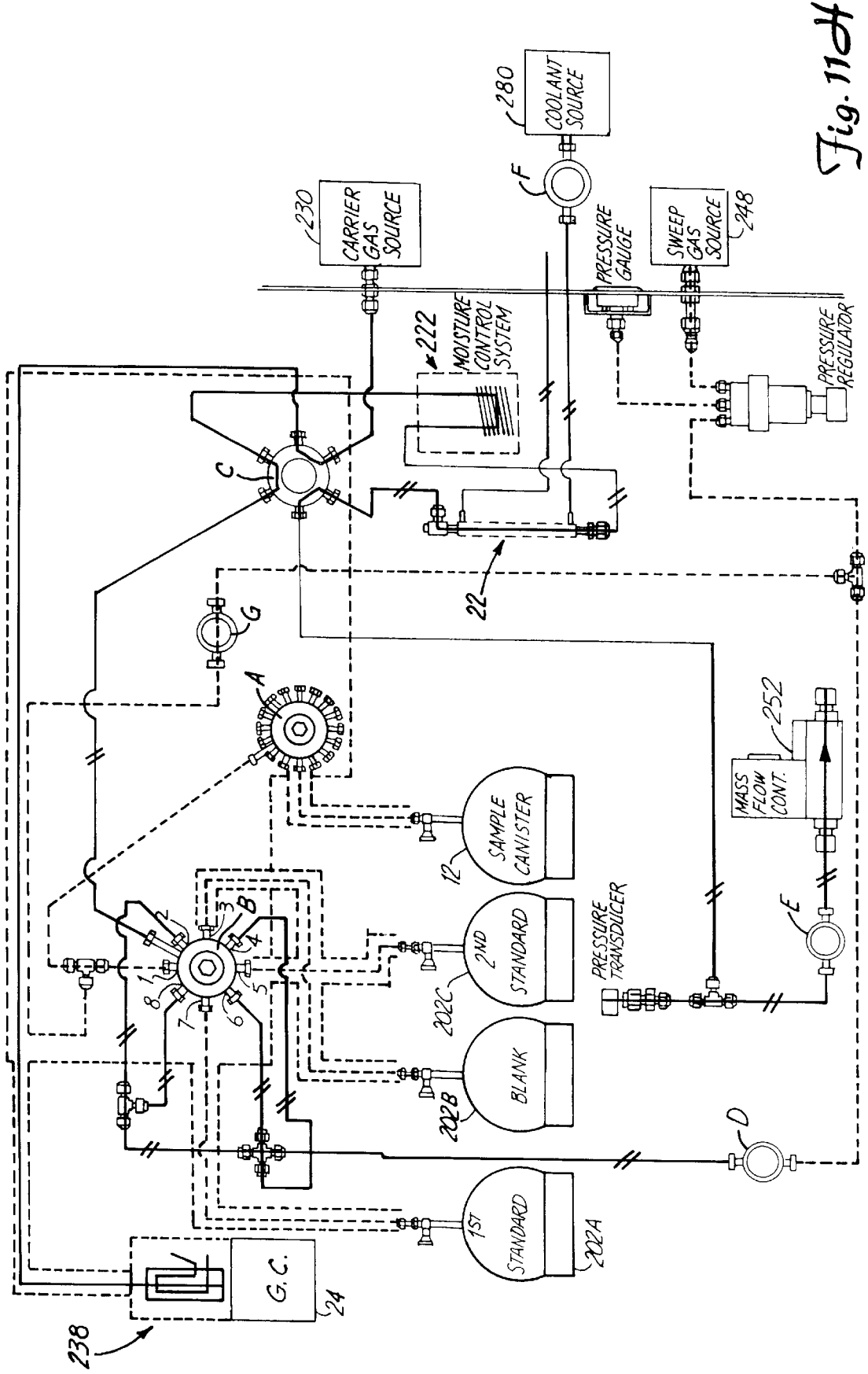

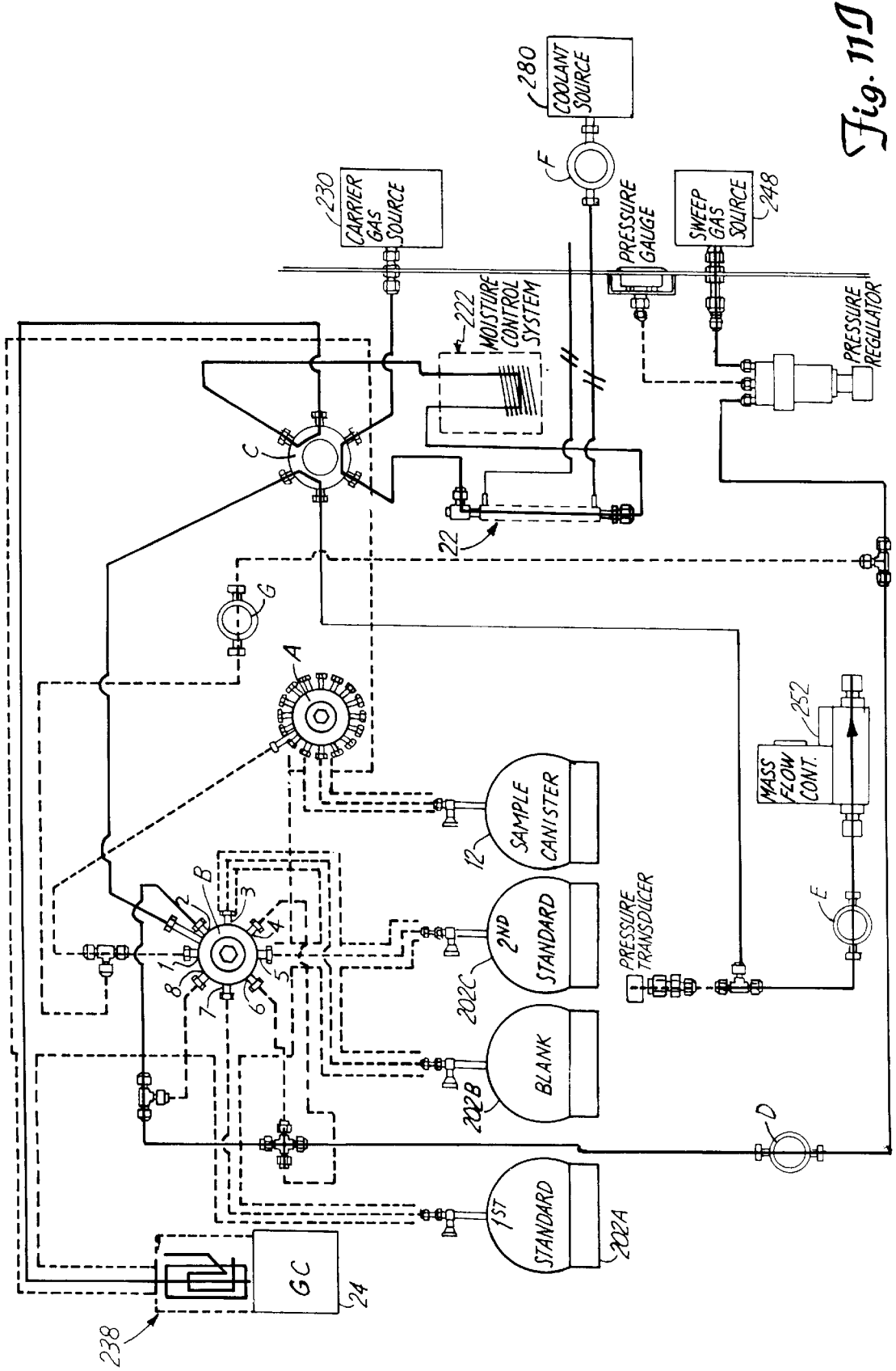

AIR SAMPLER WITH TRAP

This is a continuation of application Ser. No. 08/556,620, filed Nov. 13, 1995, now abandoned.

BACKGROUND OF THE INVENTION

The present invention relates to analytical apparatuses used for detecting for volatile organic compounds (VOCs). More particularly, the present invention relates to an apparatus and method for preparing an air sample prior to analyzing.

The identification of toxic or other undesirable volatile organic compounds (VOCs) is an ongoing requirement by many including individuals, companies and governmental entities. The use of canisters, such as SUMMA passivated canisters is one common technique. The SUMMA canisters are commonly pre-evacuated prior to being brought into the field. The air samples are then collected in the SUMMA canisters. After collection, the sample canisters are transported to a central location where they are arranged on a sampling apparatus that can selectively obtain samples from each of the canisters. The sampling apparatus is coupled to a concentrating apparatus. The concentrating apparatus receives samples from the sampling apparatus. The concentrating apparatus concentrates VOCs by collection in a reduced temperature (sorbent) trap while other components of the air sample, such as nitrogen and oxygen, are not retained. Once the VOCs have been collected in the sorbent trap, the trap temperature is elevated and a carrier gas flows through to remove the VOCs during a "desorb" step.

There is an ongoing need to simplify the analysis of air samples to reduce cost and insure reliability.

SUMMARY OF THE INVENTION

An air sampler includes a stand adapted to support sample enclosures at spaced-apart locations. A multiposition valve is mounted to the stand. The multiposition valve has a plurality of inlet ports and an outlet port selectively fluidly coupled to any of the plurality of inlet ports. A plurality of inlet lines connects the sample enclosures to the inlet ports. A concentrator trap mounted on the stand and coupled to the outlet port concentrates selected constituents from one of the sample enclosures.

Another broad aspect of the present invention includes a method of trapping and desorbing VOCs from a temperature controlled concentrator trap in a way that separates the VOCs from an undesired compound. The method comprises the steps of: trapping the VOCs and the undesired compound in the concentrator trap when the concentrator trap is at a low temperature; purging the concentrator trap when the concentrator trap is at an intermediate temperature at which the VOCs are retained and the undesired compound is released from the concentrator trap, and venting the undesired compound; and desorbing the VOCs from the concentrator trap when the concentrator trap is at a high temperature.

BRIEF DESCRIPTION OF THE DRAWINGS

FIG. 6 is a rear perspective view of the manifold heater.

FIG. 7 is a perspective view of a sorbent trap.

FIG. 10 is a schematic diagram of a second embodiment of an air sampler of the present invention.

DETAILED DESCRIPTION OF THE PREFERRED EMBODIMENTS

FIGS. 1–4 illustrate one aspect of the present invention comprising an air sampler generally indicated at 10. The air sampler 10 allows random, controlled access of the contents of sample enclosures, such as canisters 12. As used herein, the word "sample enclosure" includes any standard gas collection container such as a standard stainless steel canister (e.g. SUMMA), bags (e.g. TEDLAR), glass bottles, and the like.

Figure 1:
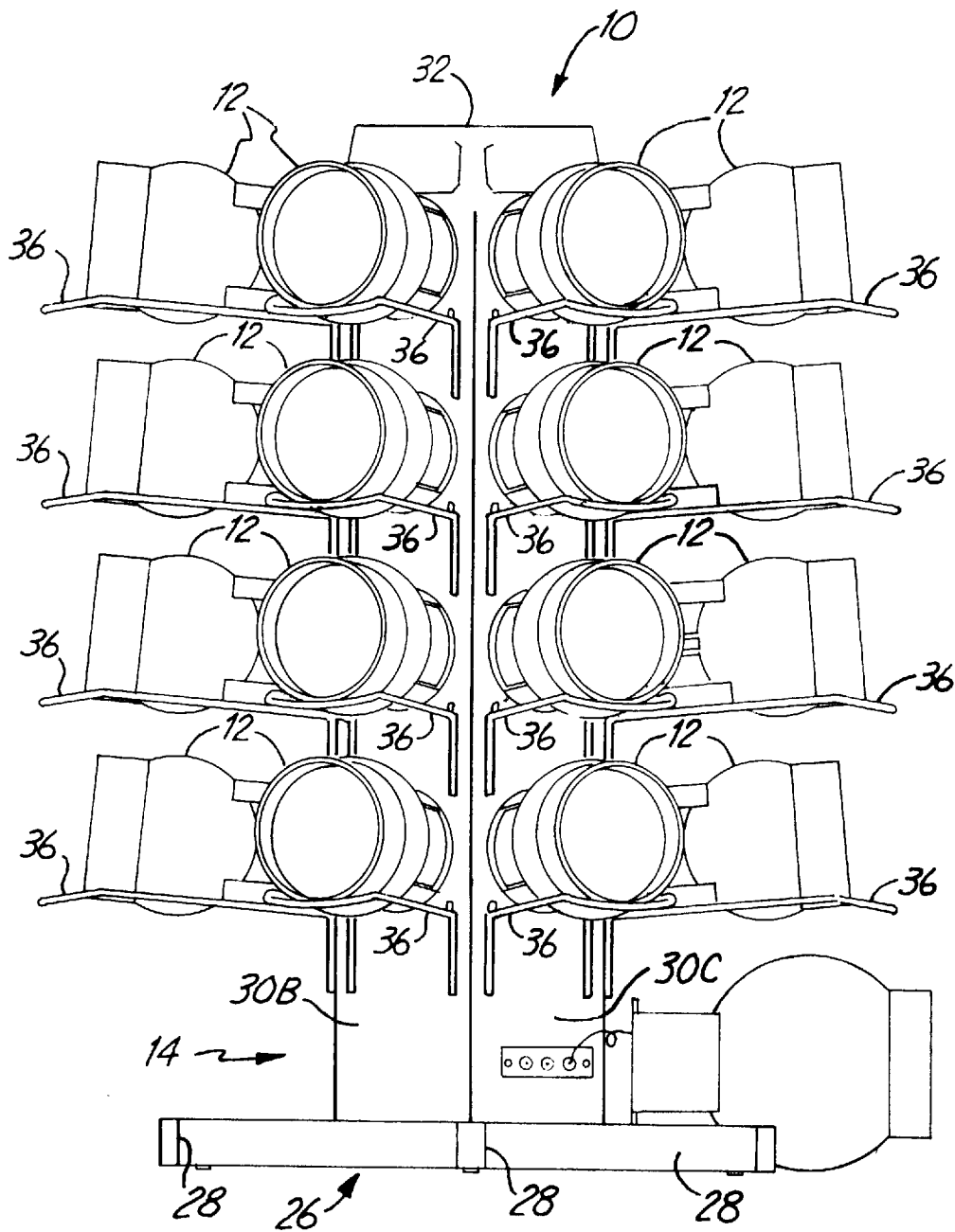
FIG. 1 is a front elevational view of an air sampler of the present invention with canisters mounted thereon.
Figure 2:
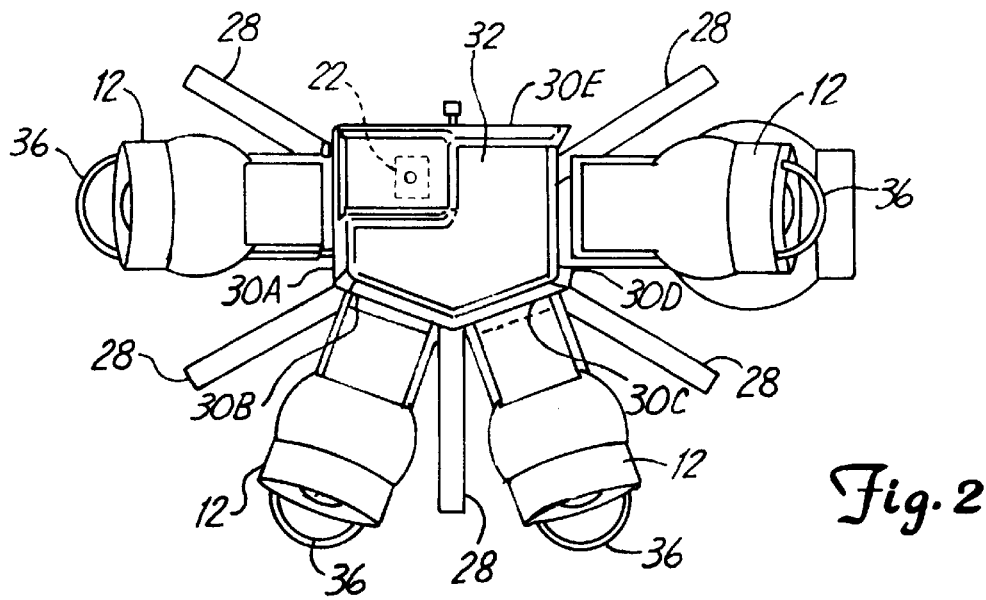
FIG. 2 is a top plan view of the air sampler of FIG. 1.
Figure 4:
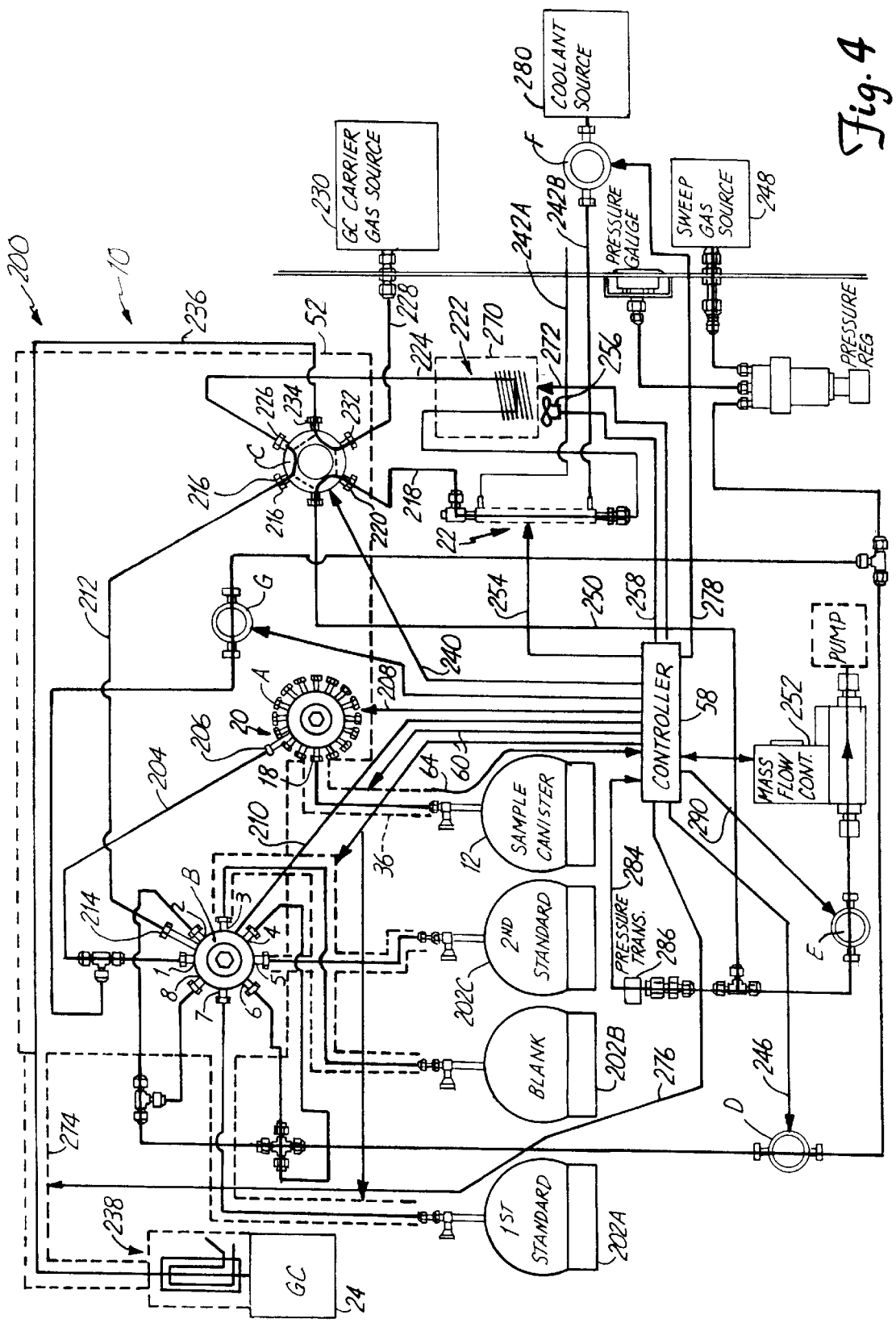
FIG. 4 is a schematic diagram of the air sampler of the present invention.

In the embodiment illustrated in FIG. 1, canisters 12 are depicted. The air sampler 10 includes a stand 14 adapted to support the canisters 12 at spaced-apart locations. Referring to FIG. 4, each of the canisters 12 are fluidly coupled to a multiposition valve A. In FIG. 4, only one canister 12 is illustrated as being fluidly coupled to the multiposition valve A at an inlet port 18. It should be understood that the remaining inlet ports, generally designated at 20, can be individually fluidly coupled to the other canisters 12. In one broad aspect of the present invention, the air sampler 10 includes a sorbent trap 22 also illustrated in FIG. 4. The sorbent trap 22 concentrates selected volatile organic compounds (VOCs) from an air sample taken from any one of the canisters 12. As will be explained below, the air sampler 10 concentrates only the VOCs and transfers the VOCs to an analytical instrument such as a gas chromatograph (GC) and/or a mass spectrometer 24 where the quantities of specific VOCs are ascertained.

Referring back to FIGS. 1–3, the stand 14 includes a base 26 formed of radially extending legs 28. Side panels 30A, 30B, 30C, and 30D extend upwardly from the base 26 and with a cover 32 form part of an enclosure for components mounted inside the stand 14. A hinged door 30E on the rear of the sampler 10 extends at least partially between the base 26 and cover 32.

A plurality of support brackets 36 are mounted on each of the side panels 30A–30D. The support brackets 36 are spaced vertically, a sufficient distance apart from each other, so that canisters 12 can pass between the support brackets 36 on which they are to rest, and any support brackets 36 located above. The side panels 30A–30D are of sufficient width so that the canisters 12 do not come into contact with each other. In the embodiment illustrated, each side panel 30A–30D carries four canisters 12 for a total capacity of sixteen (16) canisters 12. The various components of the stand 14 can be made of any material known in the art which is sufficiently strong enough to hold the canisters 12, for example, metal, wood, plastics, manufactured composite materials, and combinations there of.

In another broad aspect of the present invention, at least a portion of each inlet line that fluidly couples each canister 12 to the multiposition valve A is heated, preferably to the same temperature as valve A, approximately 200 degrees C. Heating at least a portion of the sample inlet lines helps prevent VOC adhesion or collection on inner surfaces of the sample lines, thereby increasing VOC transfer efficiency and reducing carryover.

Figure 5:
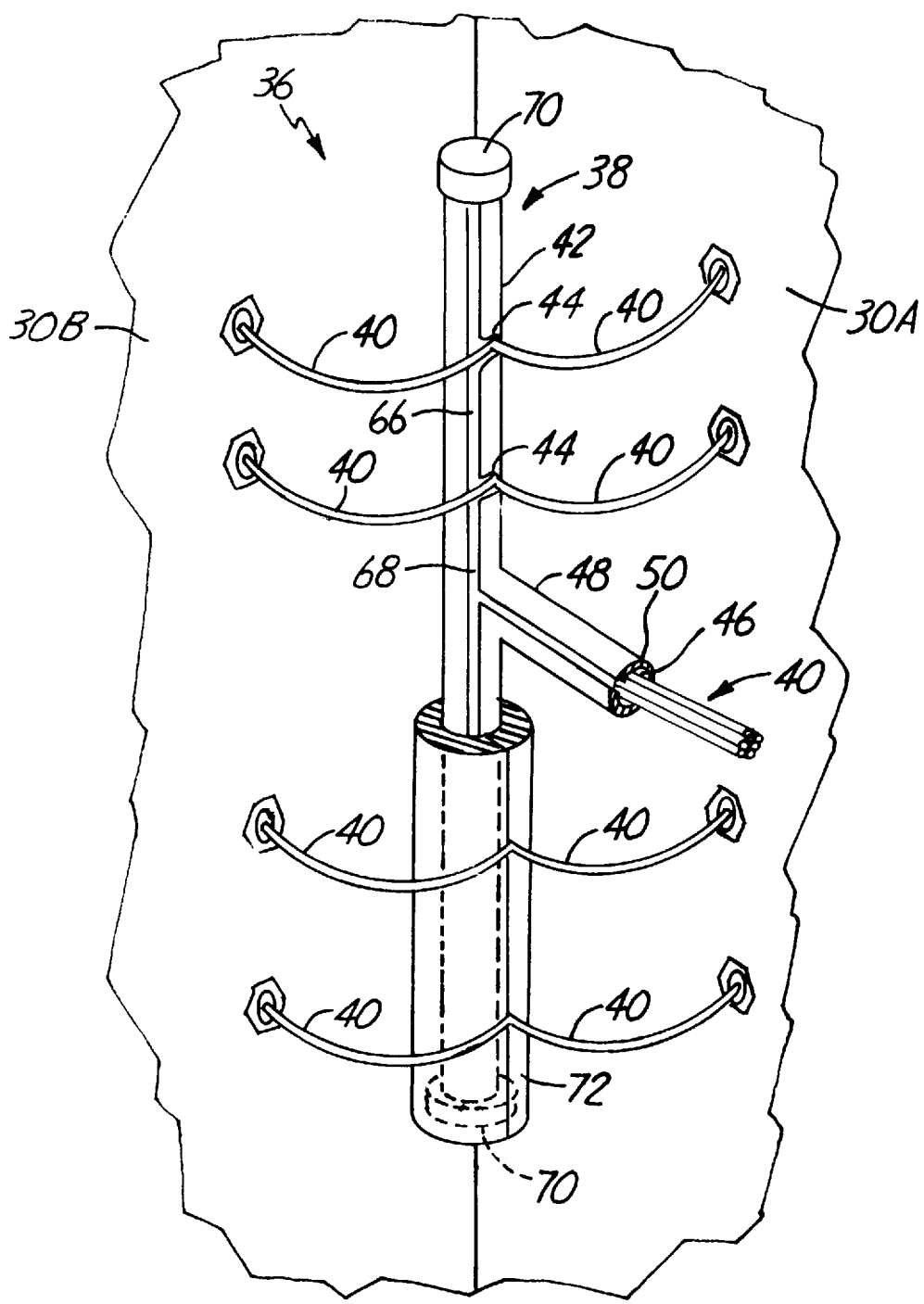
FIG. 5 is a front perspective view of a manifold heater with portions removed.

A heating assembly 36 is illustrated in FIGS. 5 and 6. The heating assembly 36 includes a manifold 38 that allow simultaneous heating of at least a portion of a plurality of inlet lines 40. In the embodiment illustrated, the manifold 38 comprises a "T-shaped", thermally conductive housing 42. Spaced-apart apertures 44 are provided in the housing 42 to allow the inlet lines 40 to extend therein. Each of the inlet lines 40 extends toward the center of the housing 42, and pass through a passageway 46 provided in a center branch 48. A remote end 50 of the center branch 48 is aligned with a corresponding aperture in an oven 52 (schematically illustrated in FIGS. 3 and 4) that is used to heat and maintain the temperature of the multiposition valve A.

In a preferred embodiment, enclosure 42 comprises copper tubing and a heater 54 is joined, preferably vulcanized, to an outer surface 56 of the enclosure 42 to transfer heat thereto as illustrated in FIG. 6. The heater 54 receives electrical power from a central controller 58 (FIG. 4) along a signal line 60. A thermocouple 62 provides a signal indicative of the temperature of the heating assembly 36 back to the controller 58 along a signal line 64.

Referring back to FIG. 5, preferably, each of the apertures 44 open to a longitudinal slot 66 that extends along the length of the enclosure 42 and along the center branch 48. The slot 66 allows the inlet lines 40 to be easily placed within the passageway 46 and within a central passageway 68 extending between the apertures 44. Metal caps 70 are provided at opposite ends of the enclosure 42 and an insulator 72 is wrapped around the enclosure 42 and the center branch 48 to provide efficient heating. Preferably, two heating assemblies 36 are provided in the apexes formed between side panels 30A and 30B, and, side 30C and 30D. In this manner, each heating assembly 36 can heat at least a portion of eight inlet lines 40 extending through the adjoining side panels. Preferably, the canisters 12 are supported on adjustable support brackets 36 and fluidly coupled to the inlet lines 40 using flexible couplers, both of which are described in detail in co-pending application entitled COUPLING OF AIR SAMPLES TO A SAMPLER, filed on the same date as the present application and incorporated herein by reference.

Figure 3:
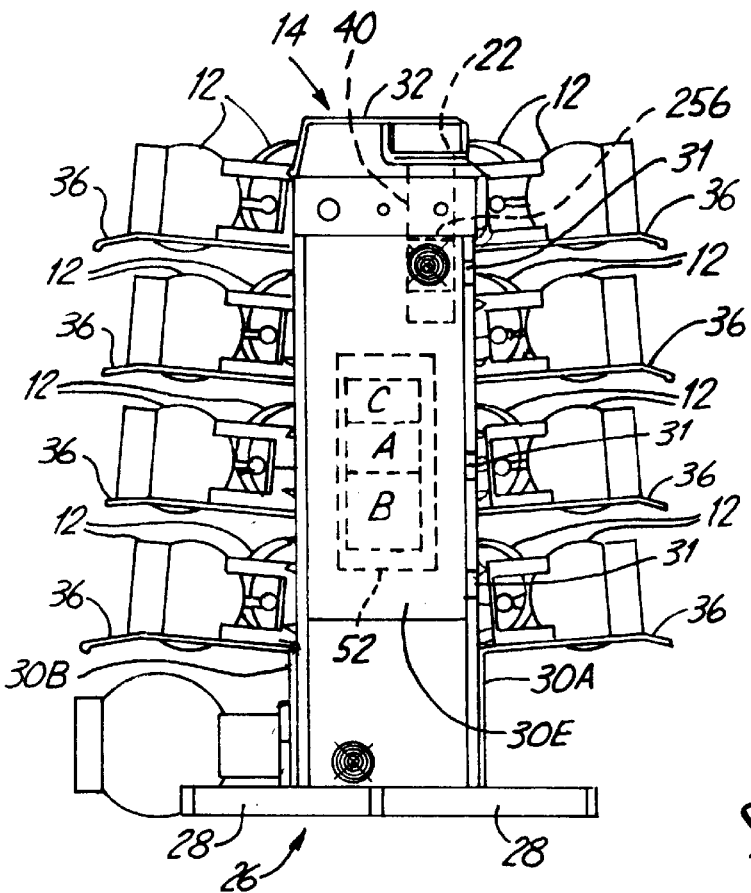
FIG. 3 is a rear elevational view of the air sampler of FIG. 1.
Figure 7A:
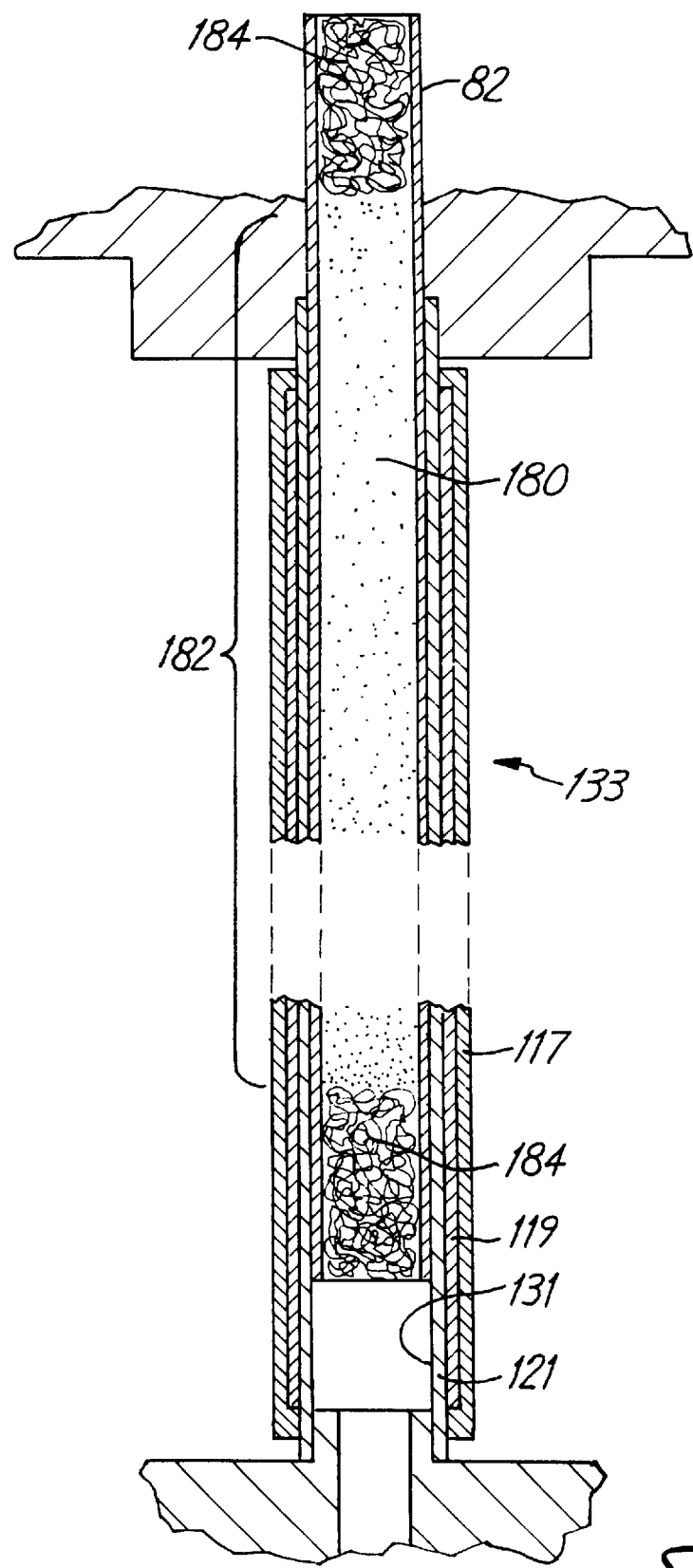
FIG. 7A is a sectional view of a sorbent trap of the present invention illustrating an inner trap tube and a trap furnace.
Figure 8:
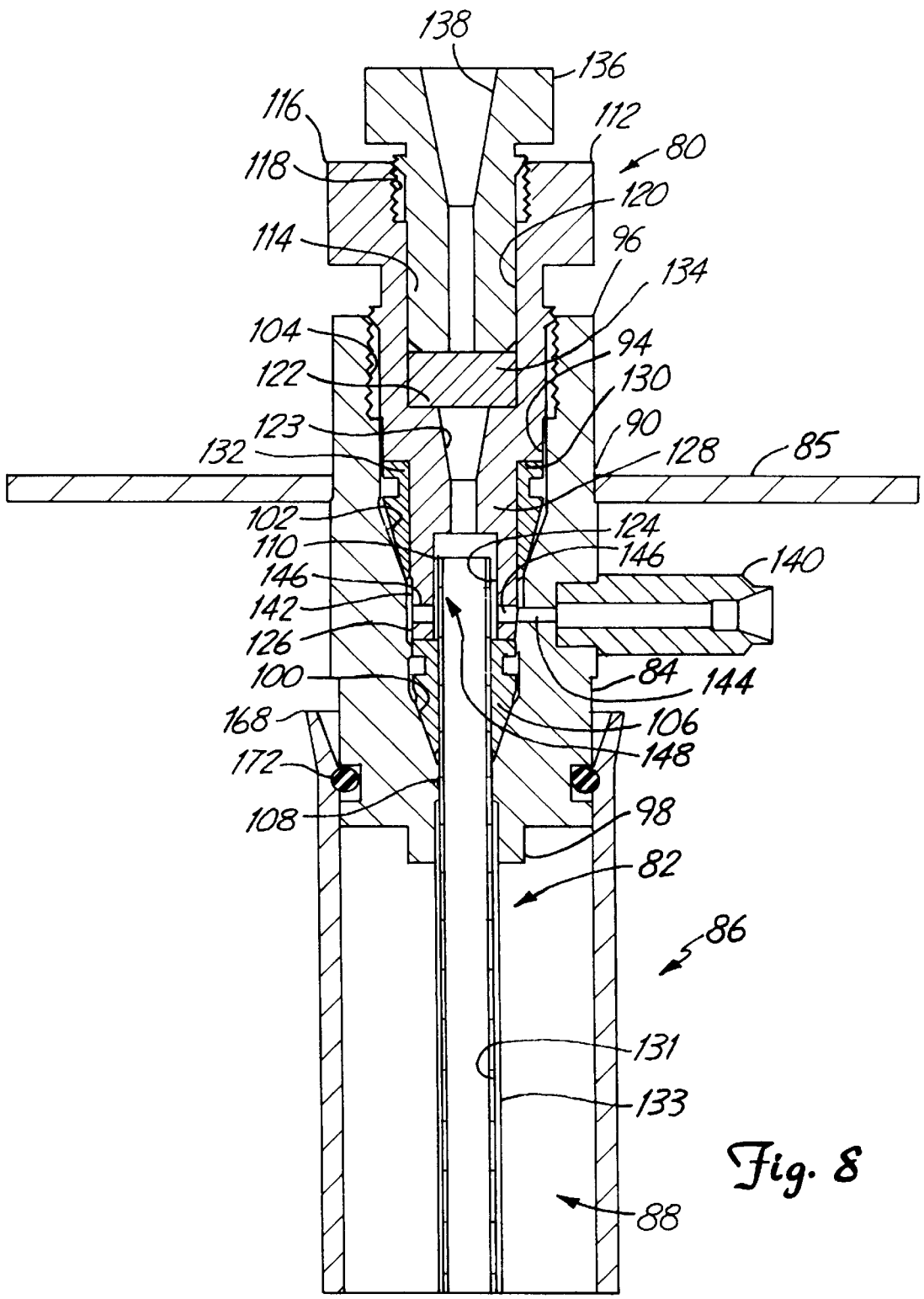
FIG. 8 is a sectional view of the sorbent trap taken along lines 8—8 in FIG. 7.
Figure 9:
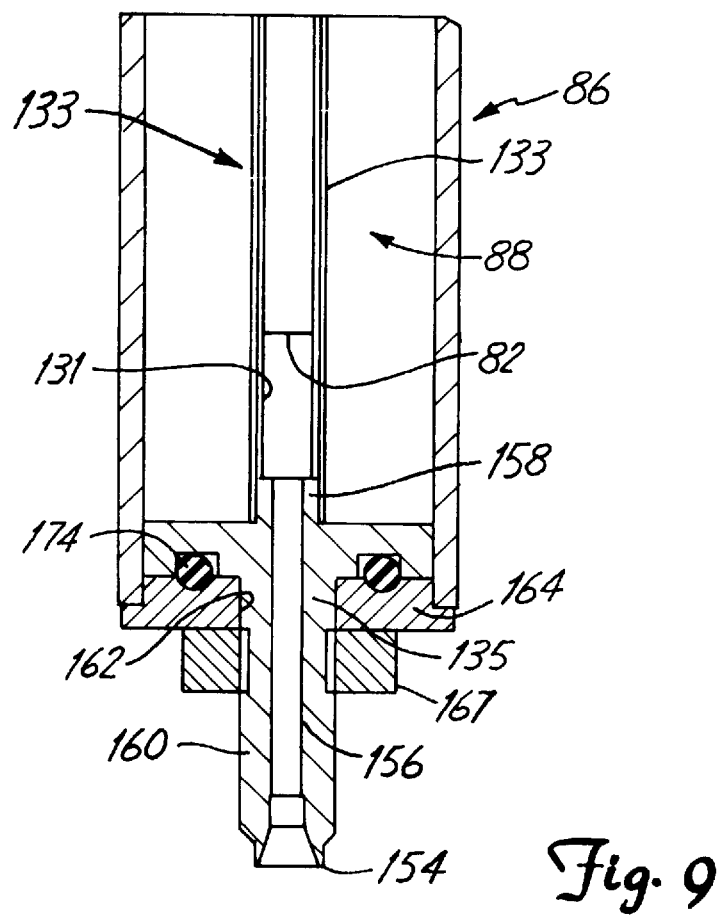
FIG. 9 is a sectional view of the sorbent trap taken along lines 9—9 in FIG. 7.

FIGS. 7–9 illustrate the sorbent trap 22, which is another broad aspect of the present invention. As will be explained below, the sorbent trap 22 includes an injection port 80 accessible from an outer surface of the stand 14. Referring also to FIG. 3, the sorbent trap 22 is vertically oriented in the stand 14 and mounts to the cover 32. Generally, the sorbent trap 22 includes an inner, replaceable, trap tube 82, a mounting hub 84 and an enclosure 86 (hereinafter "cryoenclosure 86") surrounding the trap tube 82 to form a passageway 88 (hereinafter "cryopassageway 88") in which cryogenic liquid or other coolant circulates for cooling purposes. As illustrated in FIG. 8, the mounting hub 84 extends through an aperture 90 in the cover 32. The mounting hub 84 is secured to a mounting ring 85, which in turn, is bolted to the cover 32 using conventional fasteners.

A central passageway 94 extends through the mounting hub 84 from an outer end 96 to an inner end 98 (disposed within the cryoenclosure 86). The central passageway 94 includes a first tapered or conical section 100, a second tapered or conical section 102 and a threaded portion 104 adjacent the outer end 96. The tapered portion 100 receives a ferrule 106 that is secured to an outer surface 108 of the trap tube 82, preferably, adjacent an end 110.

A nut 112 having threads which engage the threaded portion 104 of the hub 84 holds the inner trap tube 82 in place. The nut 112 has a central passageway 114 generally aligned with the passageway 94 of the hub 84. Adjacent an end 116, the nut 112 includes a threaded portion 118. The threaded portion 118 opens to, preferably, a smooth cylindrical section 120 defined by an annular stop surface 122. A tapered or conical section 123 extends from the annular stop surface 122 and opens to a second, preferably cylindrical, portion 124 that opens to end 126 of the nut 112.

As illustrated, the second cylindrical portion 124 of the passageway 114 is disposed in an extending portion 128 of the nut 112. An annular flange 130 is formed between the extending portion 128 and the rest of the nut 112. A ferrule 132 is disposed about the extending portion 128 so as to align with the tapered or conical section 102. A septum 134 seals the annular flange 122. The septum 134 is held in sealing engagement with the annular flange 122 by a nut 136 that threadable engages the threaded portion 118 of the nut 112. The nut 136 has a central passageway 138, which is generally aligned with the conical or tapered portion 123.

The injection port 80 is assembled by first inserting the trap tube 82 with the ferrule 106 there attached through the passageway 94 until the ferrule 106 contacts the conical portion 100. The ferrule 132 is then placed around the extending portion 128 of the nut 112. The nut 112 is then threaded into the hub 84. Displacement of the nut 112 into the hub 84 forces the ferrules 106 and 132 to seal adjacent surfaces of the conical portions 100 and 102, respectively. The septum 134 and the nut 136 seal the conical portion 123.

Gas exits and enters the trap 22 through a port 140. It should be understood that a diameter of the end 126 of the nut 112 is less than the corresponding diameter of the passageway 94 so as to create a cylindrical cavity 142 adjacent the end 126. The cavity 142 is sealed at opposite ends by the ferrules 106 and 132. During "desorb" mode of operation, explained below, gas enters the cavity 142 after passing through a suitable passageway 144 formed in the hub 84. After entering the cavity 142, the gas flows through suitable passageways 146 in the extending portion 128 and into the portions 123 and 124 of the passageway 114. It should be understood that a portion 148 of the inner tube 82 extending from the passageways 146 to the end 110 of the tube 82 has an outer diameter that is less than the diameter of the portion 124. This allows gas to enter the portions 123 and 124 of the passageway 114 and be forced down into the trap tube 82.

Alignment of the inner trap tube 82 with the passageway 114 of the nut 112 and the passageway 138 of the nut 136 allows a syringe needle to be inserted through the passageway 138, the septum 134 and directly into bed material located in the trap tube 82 for direct injection of known VOCs onto the trap, for diagnostic purposes. If injection of selected compounds into the inner trap tube 82 is not desired, the nut 136 can be replaced with a suitable, solid nut. In an alternative embodiment, the nut 112 can be sealed at the end 116.

Sample gases having selected compounds to be concentrated in the trap 22 enter the inner trap tube 82 through a port 154 illustrated in FIG. 9. Referring also to FIG. 7A, the inner trap tube 82, preferably made of a metal such as stainless steel, is inserted in a passageway 131 of a trap furnace 133 extending from the hub 84 to an end member 135 located at a distal end of the cryoenclosure 86. The trap furnace 133 includes a stainless steel tube 121 in which the inner trap tube 82 is placed. A resistive heating element 119 surrounds the tube 121 and is controlled by the controller 58 (FIG. 4) via a signal control line 254 to heat the trap tube 82 when desired. A ceramic outer coating 117 protects the resistive heating element 119 from cooling fluids injected into the cryopassageway 88.

Referring back to FIG. 9, the port 154 opens to the passageway 131 and the inner trap tube 82 through a passageway 156 formed in the end member 135. The end member 135 includes an extending portion 158 that is joined to the tube 121. As illustrated, the end member 135 includes an extending portion 160 that is disposed through an aperture 162 in an end cap 164 of the cryoenclosure 86. The cryoenclosure 86 is secured in place by a nut 167 that threadably engages the extending portion 160. The cryoenclosure 86 is thus easily replaced when necessary by simply removing the nut 167 and withdrawing the cryoenclosure 86 until an end 168 (FIG. 8) clears the port 154. Suitable tubes 170A and 170B allow coolant fluid to enter and exit the cryoenclosure 86, while o-rings 172 and 174 seal the cryopassageway 88 at each end of the trap 22.

Another broad aspect of the present invention is illustrated in FIG. 7A. In particular, the inner trap tube 82 is filled with a sorbent material 180 consisting essentially of Graphitized Carbon Base Sorbents (GCBS). In traps of the prior art, the trap tubes have commonly used glass beads by themselves, or in combination with other sorbent materials capable of trapping and efficiently releasing VOC compounds. Not until the present invention, has it been discovered, or has it been appreciated, that a sorbent material consisting essentially of a GCBS bed 182 is capable of trapping and efficiently releasing VOC compounds. The bed 182 is preferably held in place within the inner trap tube 82 with a suitable amount of glass wool 184 packed in each end of the inner trap tube 82. It should be understood that the present invention includes multiple sorbent material traps having a sorbent bed consisting, essentially, of GCBS material where trapping of the VOC compounds occurs. In other words, a multiple layer sorbent trap having sorbent material layers other than GCBS material, but where the other sorbent material layers do not trap any VOC compounds during operation, is, in fact, a sorbent trap of the present invention.

Table I below provides a list of VOCs that can be concentrated in the sorbent trap 22 utilizing the GCBS bed 182.

TABLE I

Bromochloromethane
Dichlorodifluoromethane
Chloromethane
Dichlorotetrafluoroethane
Vinyl Chloride
Bromomethane
Chloroethane
Ethanol
Tricholorofluoromethane
Acetone
Isopropyl Alcohol
Diethyl Ether
1,1, Dichloroethene
Acrylonitrile
Freon 113
Methylene Chloride
Allyl Chloride
n-Propanol
MTBE
1,1-Dichloroethene
Chloroform
Isobutanol
Tetrahydrofuran
1,1,1-Trichloroethane
1,2-Dichloroethane
n-Butanol
Benzene
Carbon Tetrachloride
1,4-Difluorobenzene
1,2 Dichloropropane
Trichloroethene
Methyl Methacrylate
MIBK
c-1,3-Dichloropropene
t-1,3-Dichloropropene
Toluene
1,1,2-Trichloroethane
Ethyl Methacrylate
2-Hexanone
1,2-Dibromoethane
Tetrachloroethene
d5-Chlorobenzene
Chlorobenzene
m,p-Zylene
2-Heptanone
Styrene
o-Zylene
1,1,2,2-Tetrachloroethane
4-Bromofluorobenzene
4-Ethyltoluene
1,3,5-Trimethylbenzene
1,2,4-Trimethylbenzene
1,3-Dichlorobenzene
1,3-Dichlorobenzene
1,2,4-Trichlorobenzene
Hexachlorobutadiene Of course, compounds of similar chemistry can also be collected using the GCBS bed. The sorbent trap of the present invention can be operated at relatively high temperatures (e.g. −100 to −65 degrees C.) during the sample and standard transfer modes compared to glass bead traps (−190 to −165 degrees C.), thus less coolant is required by the sorbent trap of the present invention.

FIG. 4 illustrates components of the air sampling system 10 of the present invention with interconnecting gas flow lines generally indicated at 200. Before describing various operating modes illustrated in FIGS. 11A–11N, a brief description of the air sampling system 10 illustrated in FIG. 4 will be helpful.

The air sampling system 10 obtains samples from any of the canisters 12 and collects any VOCs therein in the sorbent trap 22. The collected selected compounds from the sorbent trap 22 are "desorbed" from the sorbent trap 22 and transferred to the gas chromatograph 24 for analysis.

The multiposition valve A, a second multiposition valve B, and a third multiposition valve C fluidly couple the canisters 12, and one or more canisters 202A, 202B and 202C, containing reference standards of known constituents with the sorbent trap 22 and the gas chromatograph 24. As illustrated, the multiposition valve B is fluidly coupled to each of the reference standard canisters 202A–202C at import ports 7, 3 and 5, respectively. A gas line 204 couples an outlet port 206 of the multiposition valve A and an inlet port 1 of the multiposition valve B. The controller 58 provides control signals to the multiposition valve A along a signal line 208 and to the multiposition valve B along a signal line 210 to select any one of the reference standard canisters 202A–202C or any one of the canisters 12. The controller 58 receives status signals from the gas chromatograph 24.

A gas line 212 fluidly couples an outlet port 214 of the multiposition valve B to an inlet port 216 of the multiposition valve C. As illustrated, the multiposition valve C has six ports wherein each port is selectively fluidly connected separately to two adjacent ports. A first position is illustrated with solid lines and a second position is illustrated with dashed lines. A gas flow line 218 fluidly couples a port 220 of the multiposition valve C to the port 140 of the sorbent trap 22. The port 154 of the sorbent trap 22 is fluidly coupled through a moisture control system indicated at 222 and through a gas flow line 224 to a port 226 of the multiposition valve C. Moisture control systems are known. A suitable moisture control system is used in the Model 3000 Purge and Trap Concentrator, commercially available from Tekmar Company of Cincinnati, Ohio, and described in the corresponding owner manual, which is incorporated herein by reference. The moisture control system 222 is maintained at a single temperature (e.g. 50 degrees C.) during all modes of operation, except a "Bake/Inject" mode, when it is heated to several hundred degrees C.

A gas flow line 228 couples a source of carrier gas 230 to a port 232 of the multiposition valve C. A gas flow line 236 couples a port 234 of the multiposition valve C to the gas chromatograph 24. As illustrated, an optional sorbent trap 238 can be fluidly coupled between the gas flow line 236 and the gas chromatograph 24 for cryofocusing.

In operation, the controller 58 provides suitable control signals to the multiposition valve A, to the multiposition valve B, and to the multiposition valve C along a signal line 240 to fluidly couple the sorbent trap 22 to the reference standard canisters 202A–202C and any one of the canisters 12. The sorbent trap 22 receives cooling fluid through cooling lines 242A and 242B to cool the sorbent trap 22, and thus, collect the VOCs. After the VOCs have been concentrated in the sorbent trap 22, the controller 58 can operate the multiposition valve B and a valve D via a signal line 246 to allow a suitable sweep gas to flow from a sweep gas source 248, through one of the inlet ports 2, 4, 6 or 8 of the multiposition valve B, through the multiposition valve C (operated in the position illustrated with solid lines), through the sorbent trap 22 and out through a gas flow line 250, through a valve E and to a mass flow controller 252. This operating state is often called a "drypurge" because moisture and other selected compounds such as $CO_2$ are removed from the sorbent trap 22. During the drypurge step, or immediately prior to it, the controller 58 activates the trap furnace 133 via the signal line 254 to heat the sorbent trap 22.

After the drypurge step, the temperature of the sorbent trap 22 is increased and carrier gas directed therethrough so as to "desorb" the VOCs. The controller 58 operates the multiposition valve C to the position illustrated with dashed lines in order that the carrier gas from the carrier gas source 230 is passed through the sorbent trap 22 and to the gas chromatograph 24 via the gas flow line 236.

The moisture control system 222 is selectively heated through a heater 270, which is controlled by the controller 58 through a signal line 272, or cooled by a fan 256 via a signal line 258 so as to maintain a desired temperature. A heater 274 heats a portion of the line 236 not within the oven 52. The controller 58 controls the heater 274 via signal line 276. The controller 58 also controls a valve F through a signal line 278 that allows coolant to flow to the sorbent trap 22 from a coolant source 280, typically liquid nitrogen. The controller 58 receives a signal along a signal line 284 from a pressure transducer 286 indicative of the pressure in the line 250. A valve E controls fluid flow through the line 250 and is controlled by the controller 58 via a signal line 290.

Referring back to FIG. 3, the fan 256 (indicated with dashed lines) is mounted to the hinged door 30E so as to align with a coiled portion of the moisture control system 222 when the hinged door 30E is closed. The fan 256 is mounted proximate hinges 31 of the hinged door 30E to minimize the length required for the corresponding power lines for the fan 256.

Figure 11A:
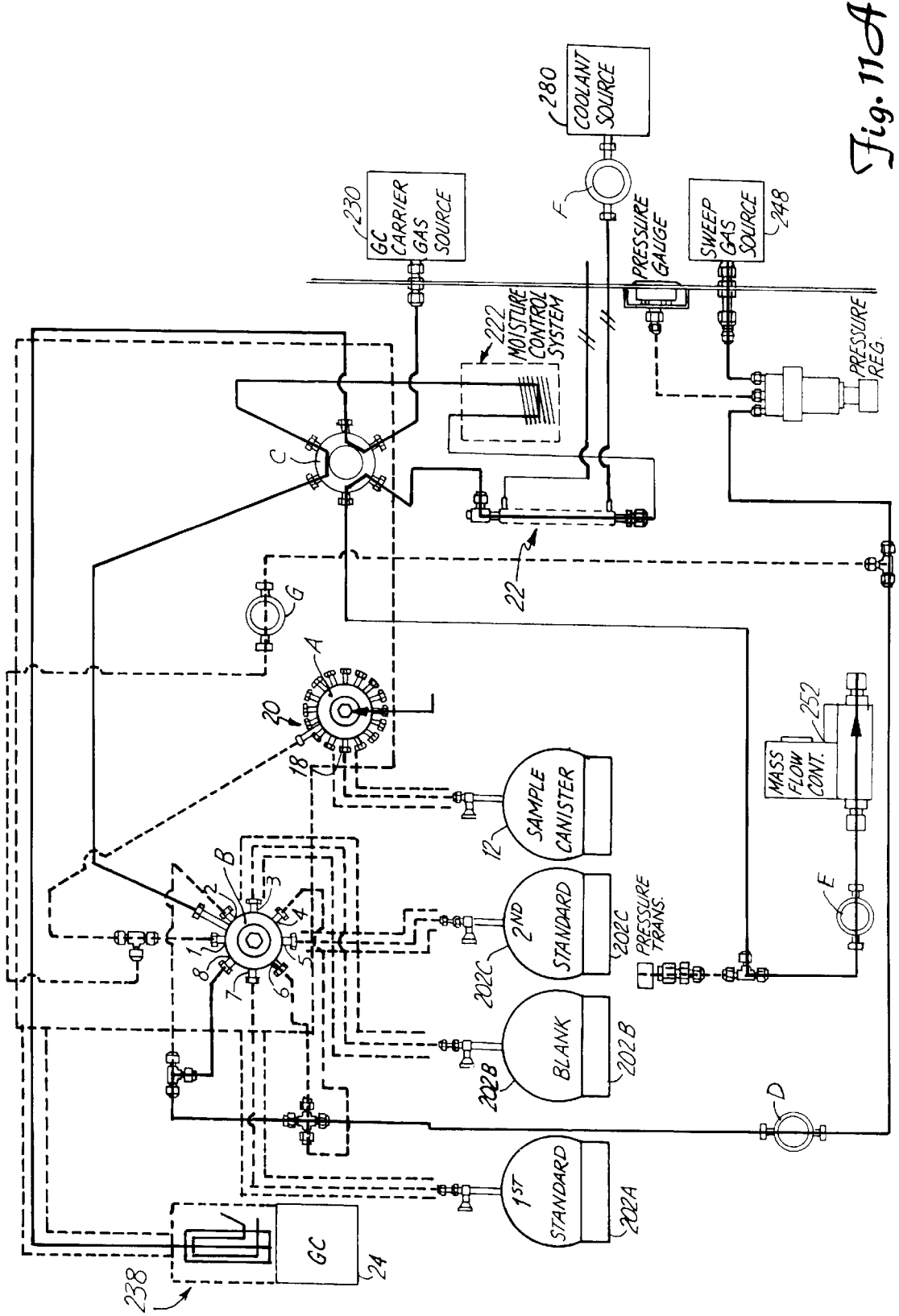
FIGS. 11A–11N are schematic drawings illustrating gas flow through components of the air sampler of the present invention of FIG. 4 in various operating modes.
Figure 11B:
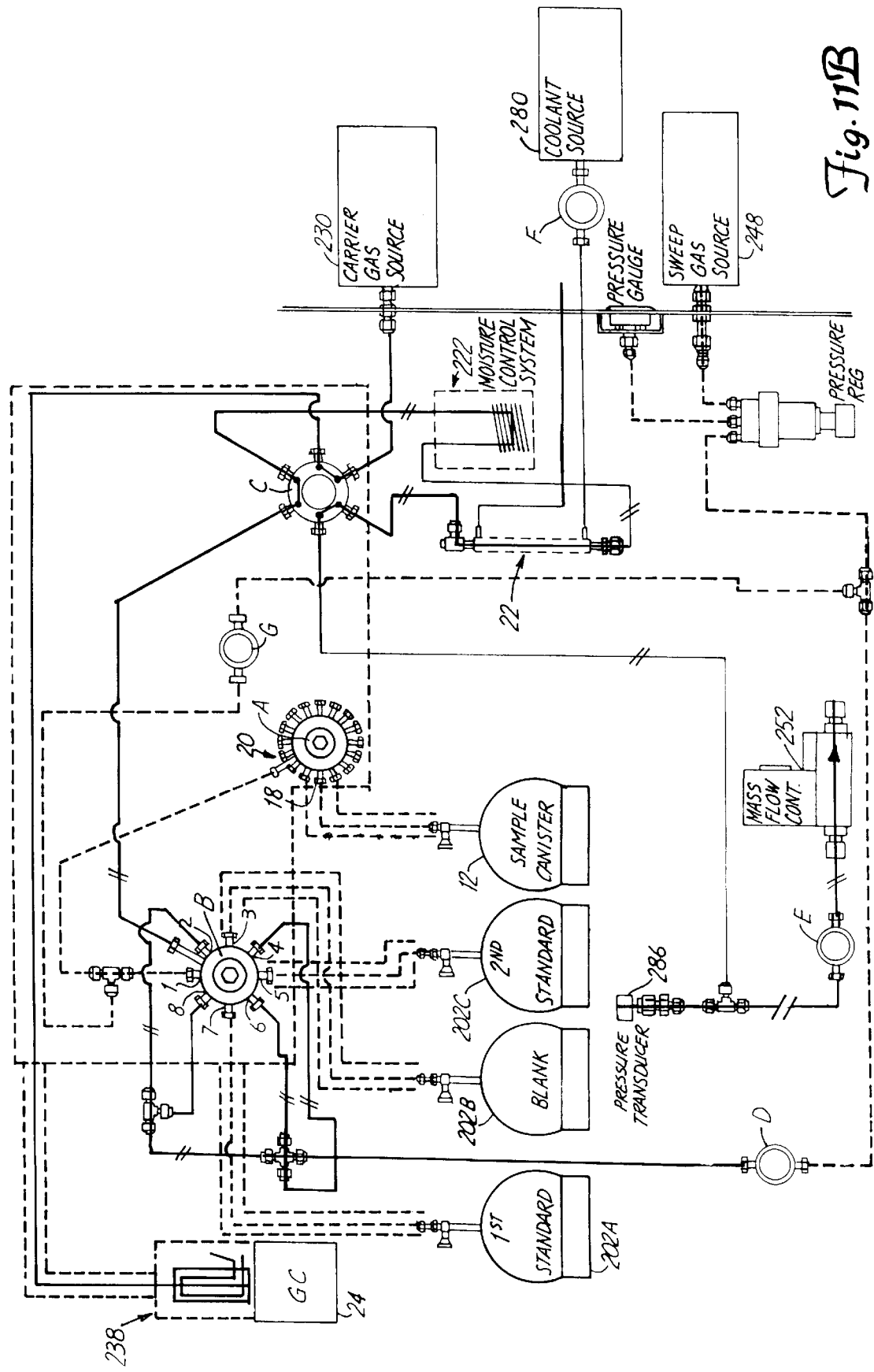
Figure 11C:
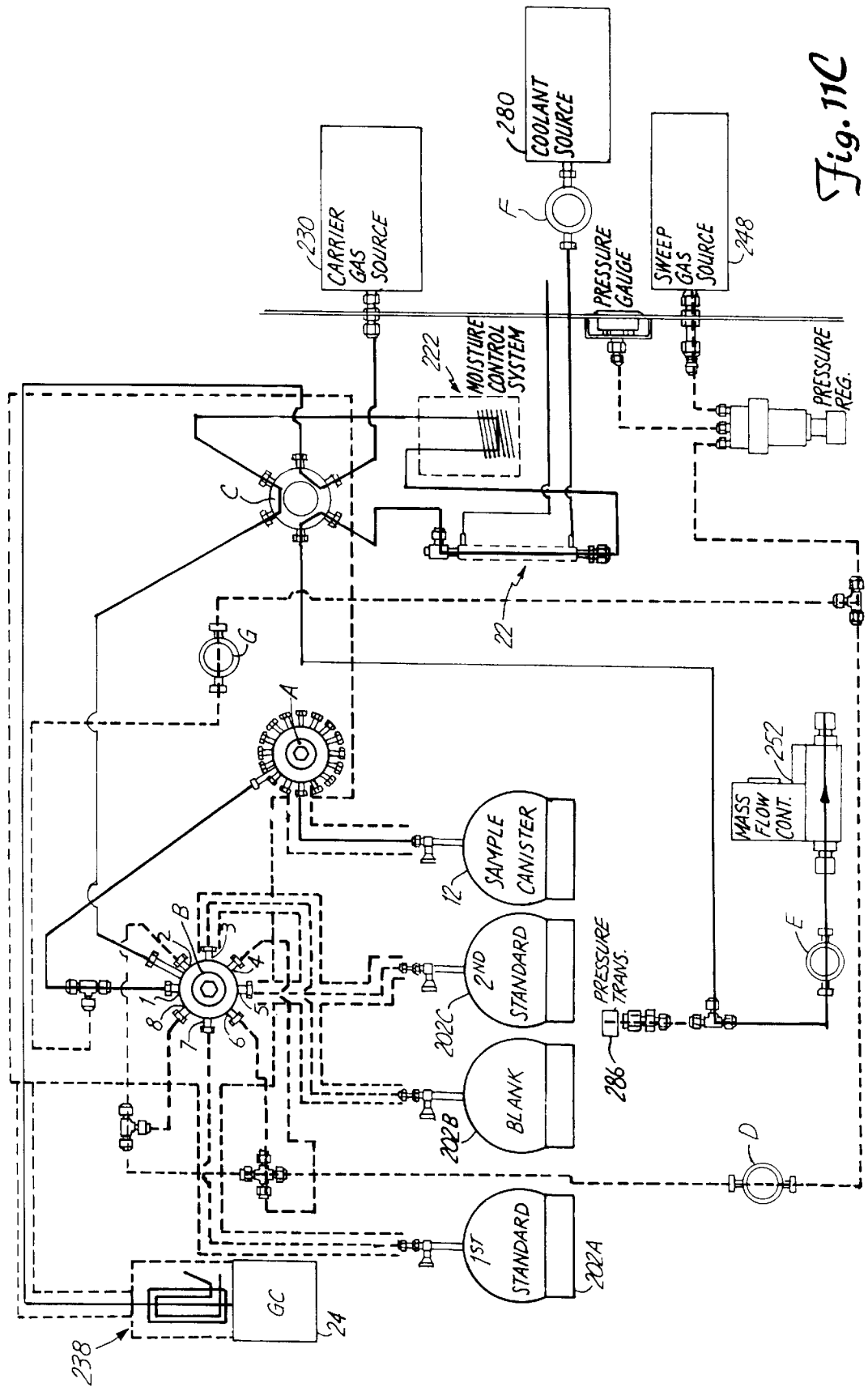
Figure 11D:
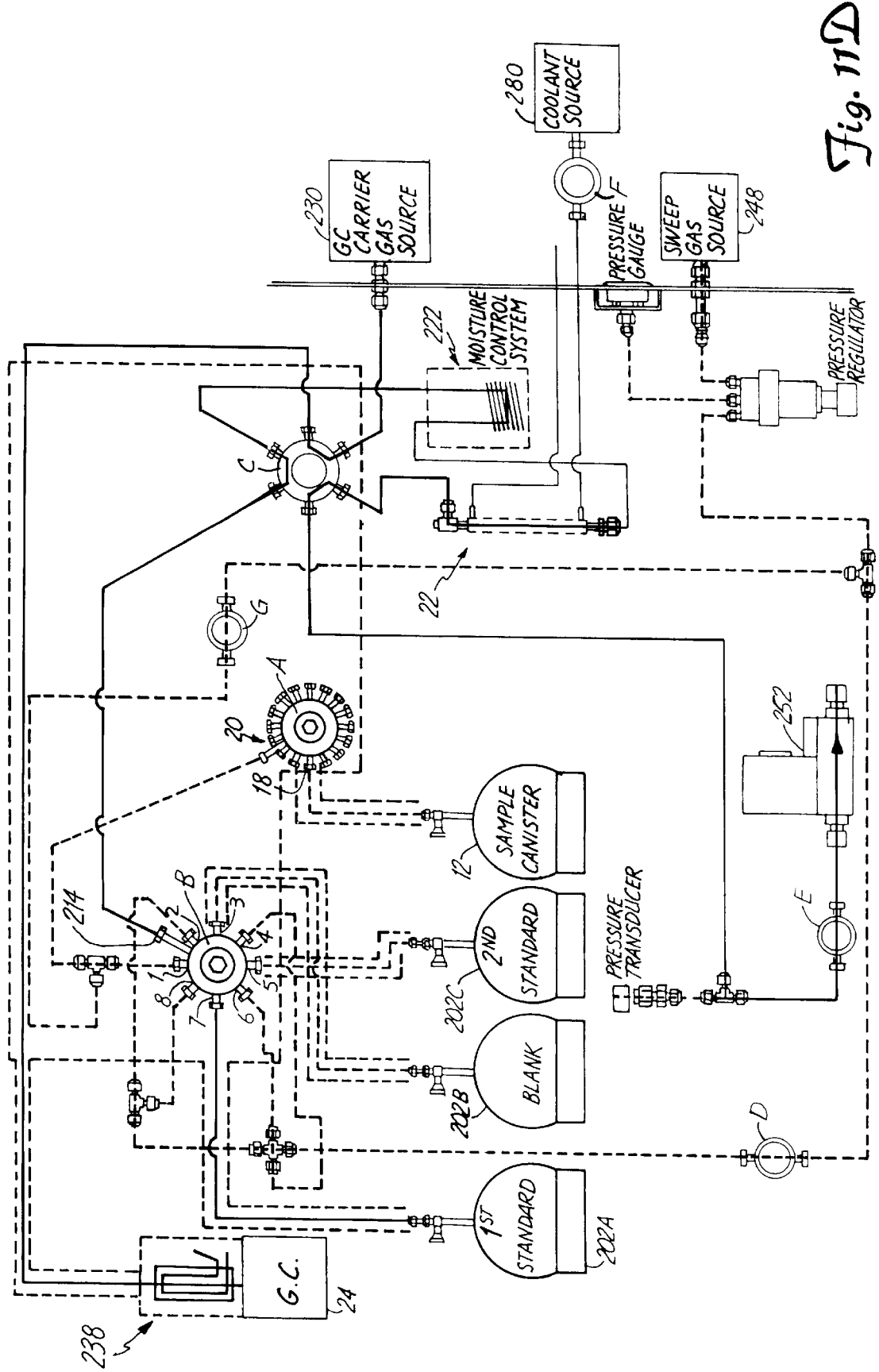
Figure 11E:
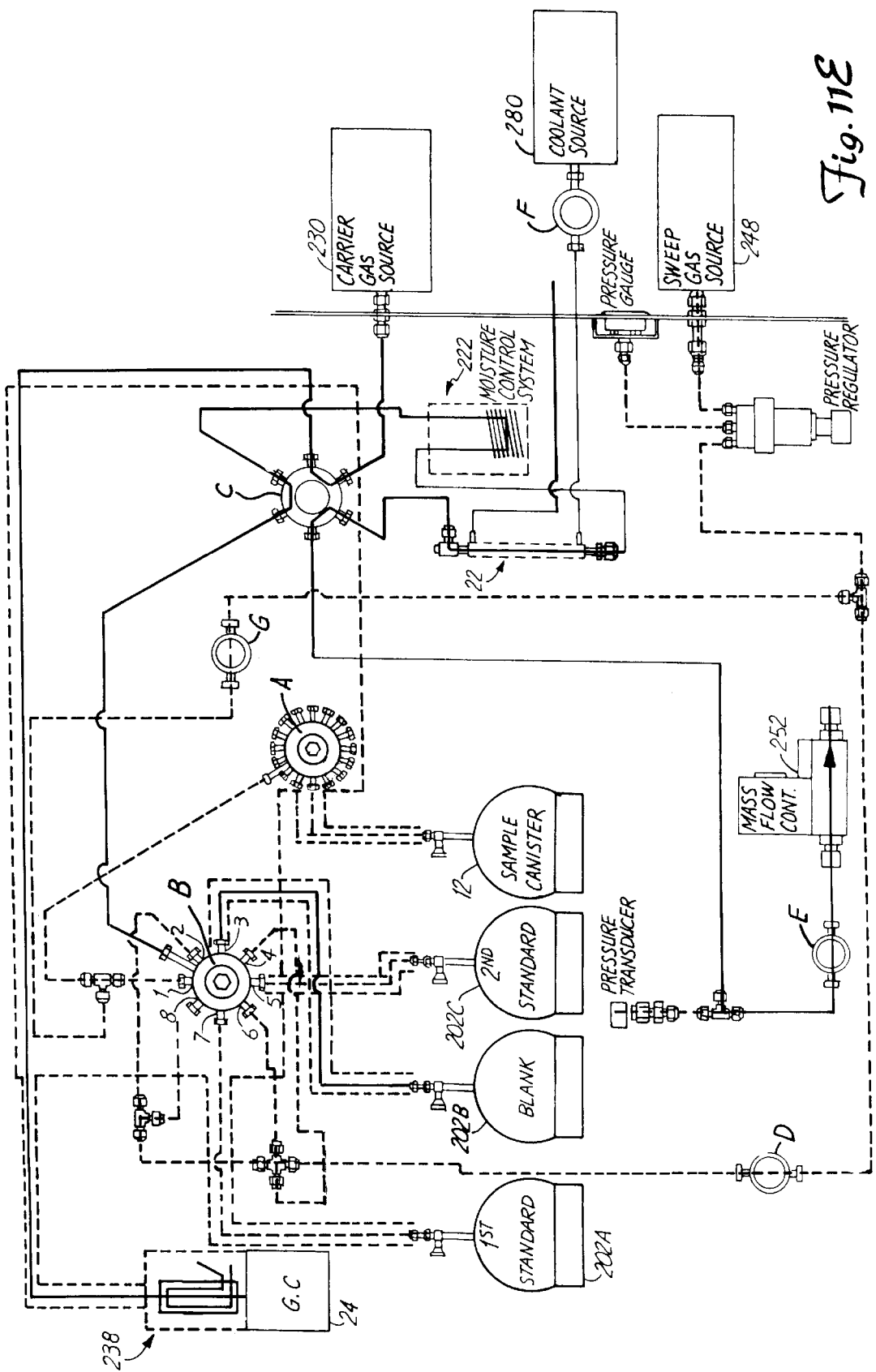
Figure 11F:
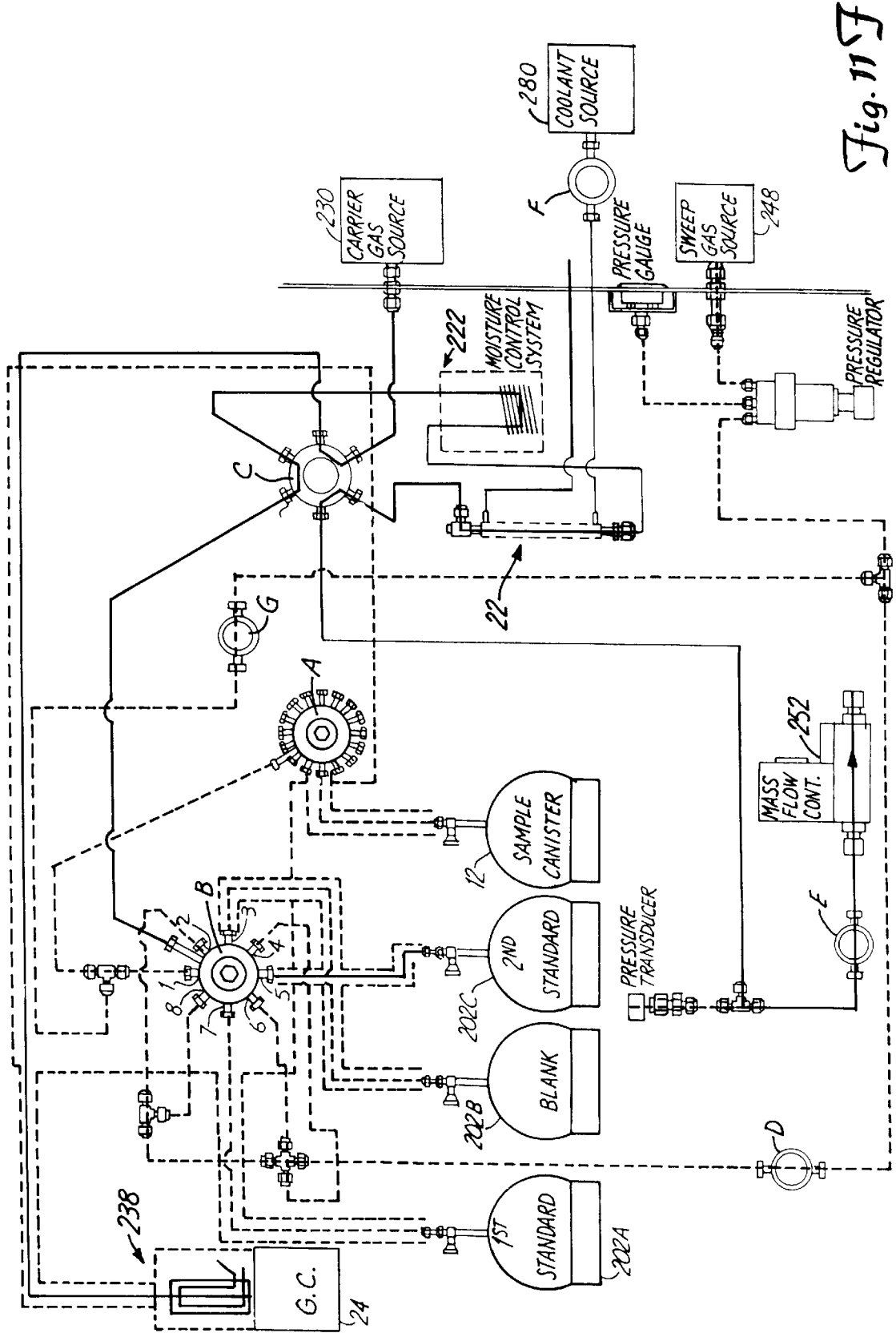
Figure 11G:
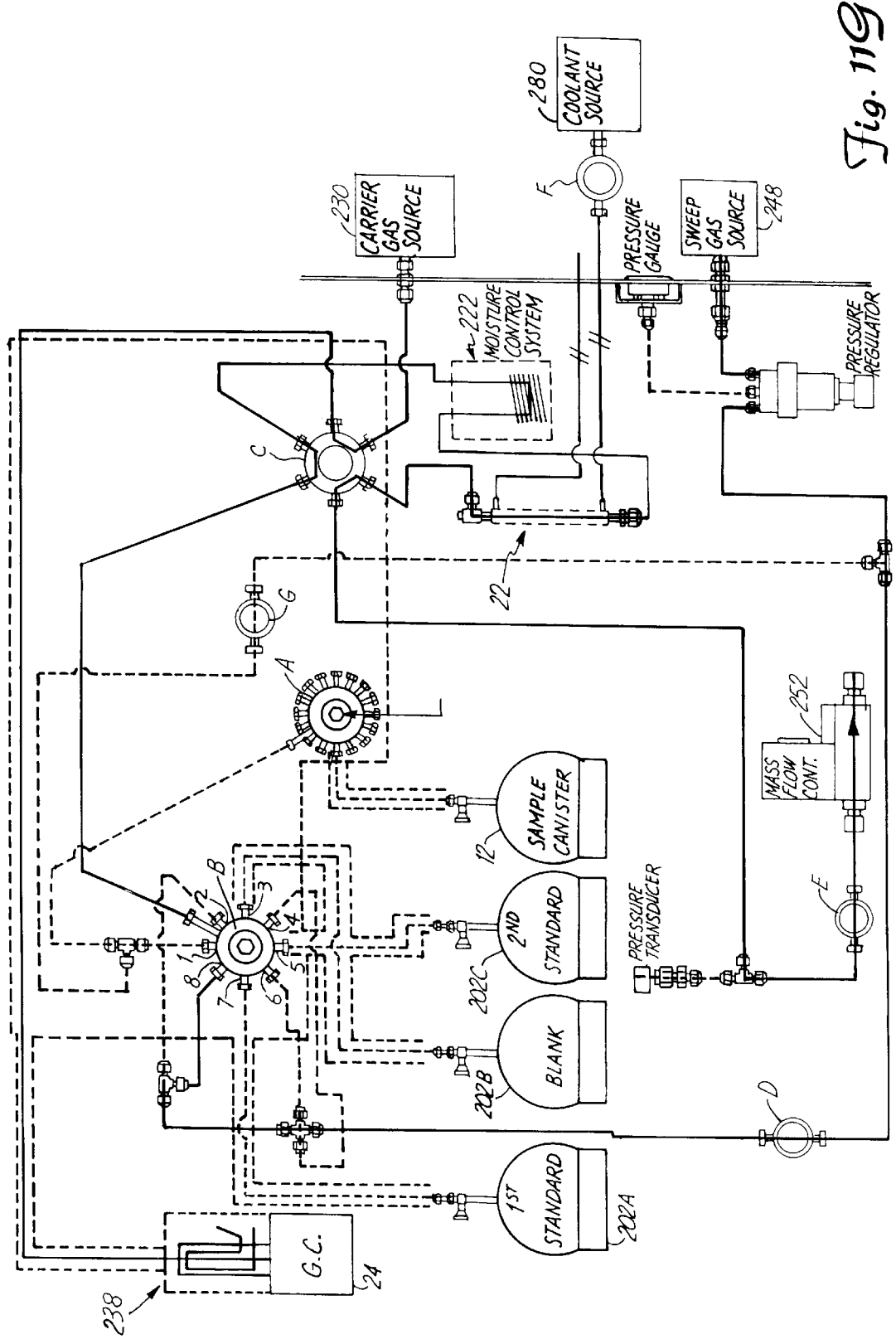
Figure 11A:
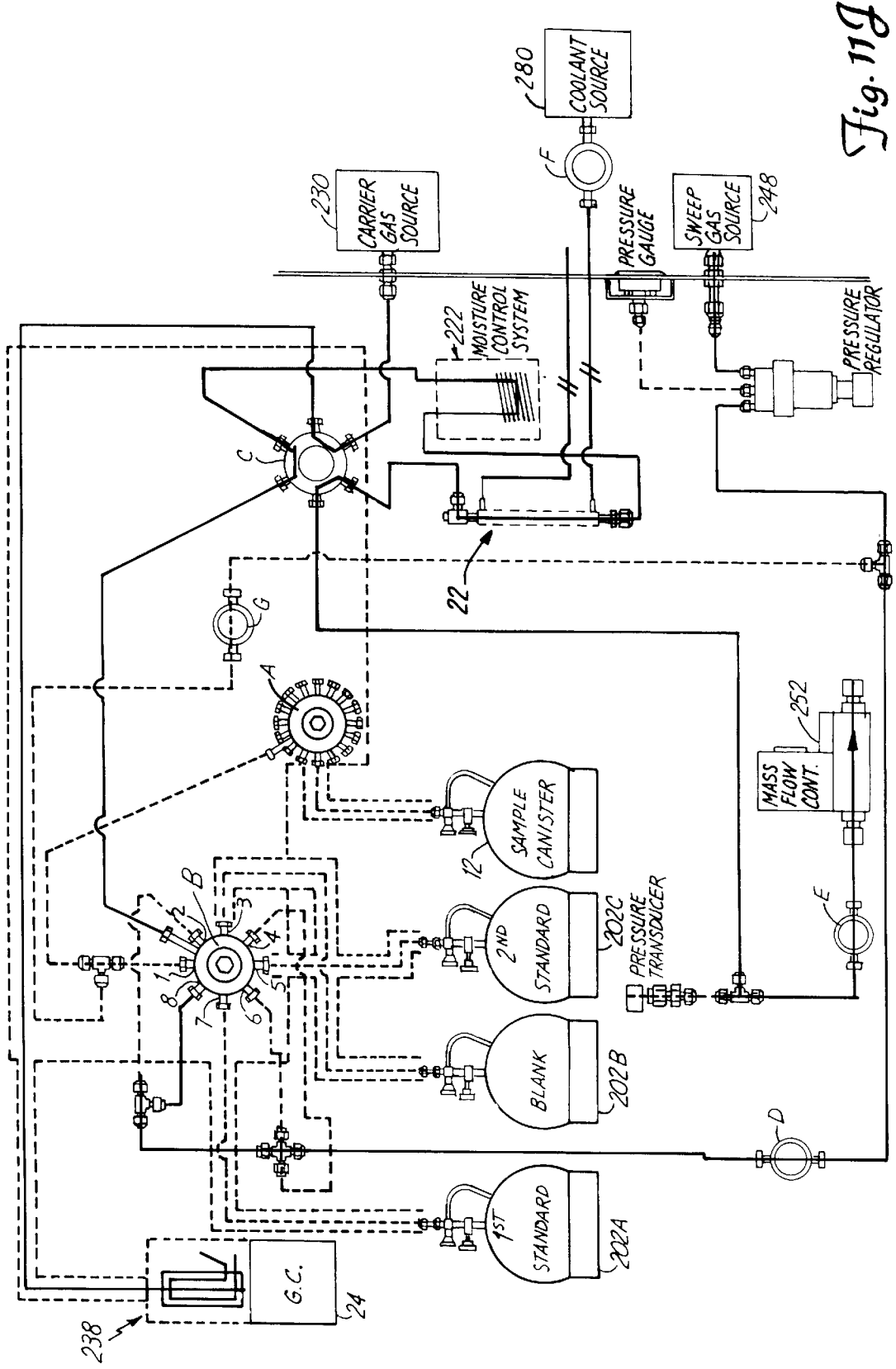
Figure 11K:
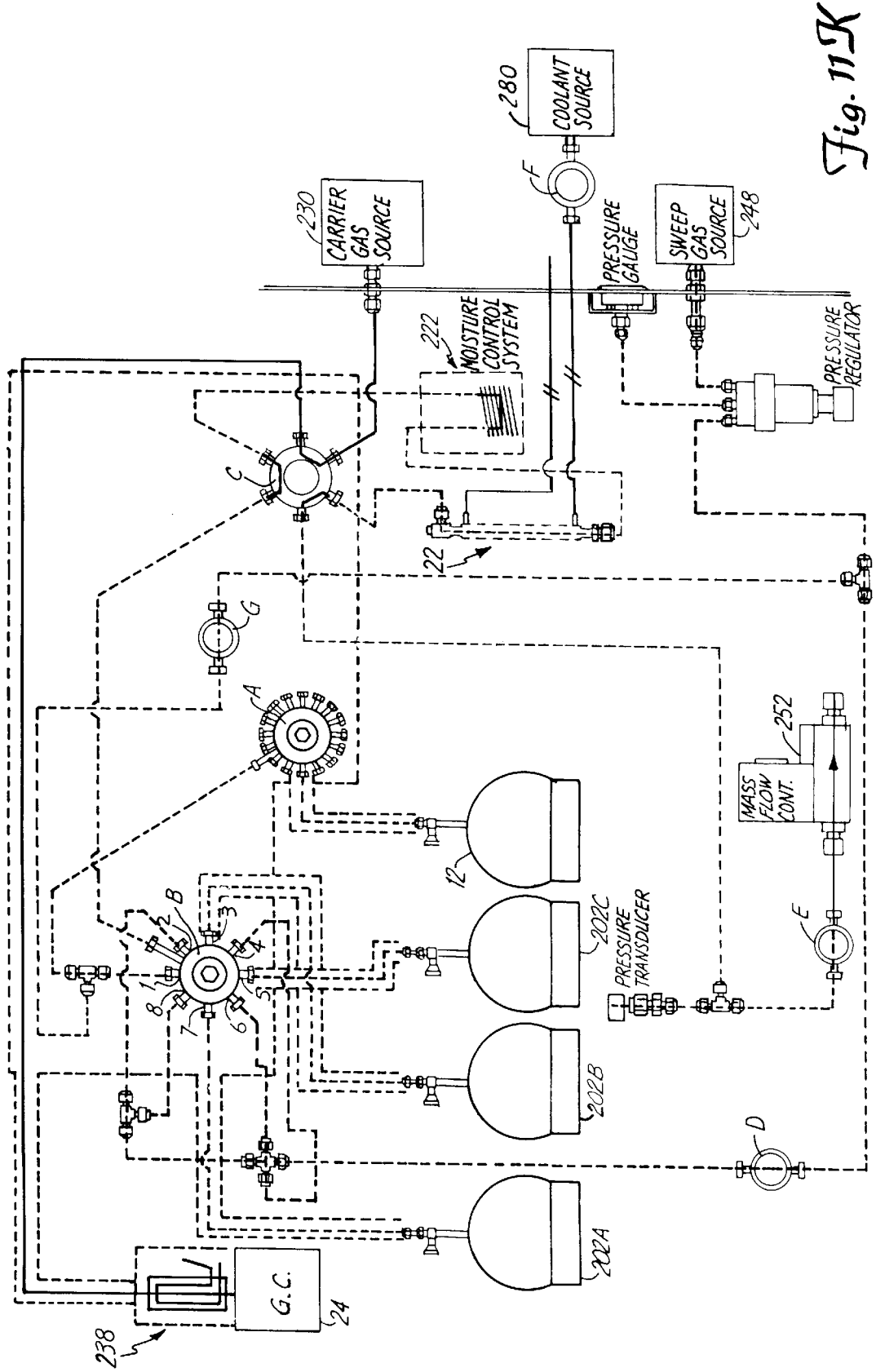
Figure 11L:
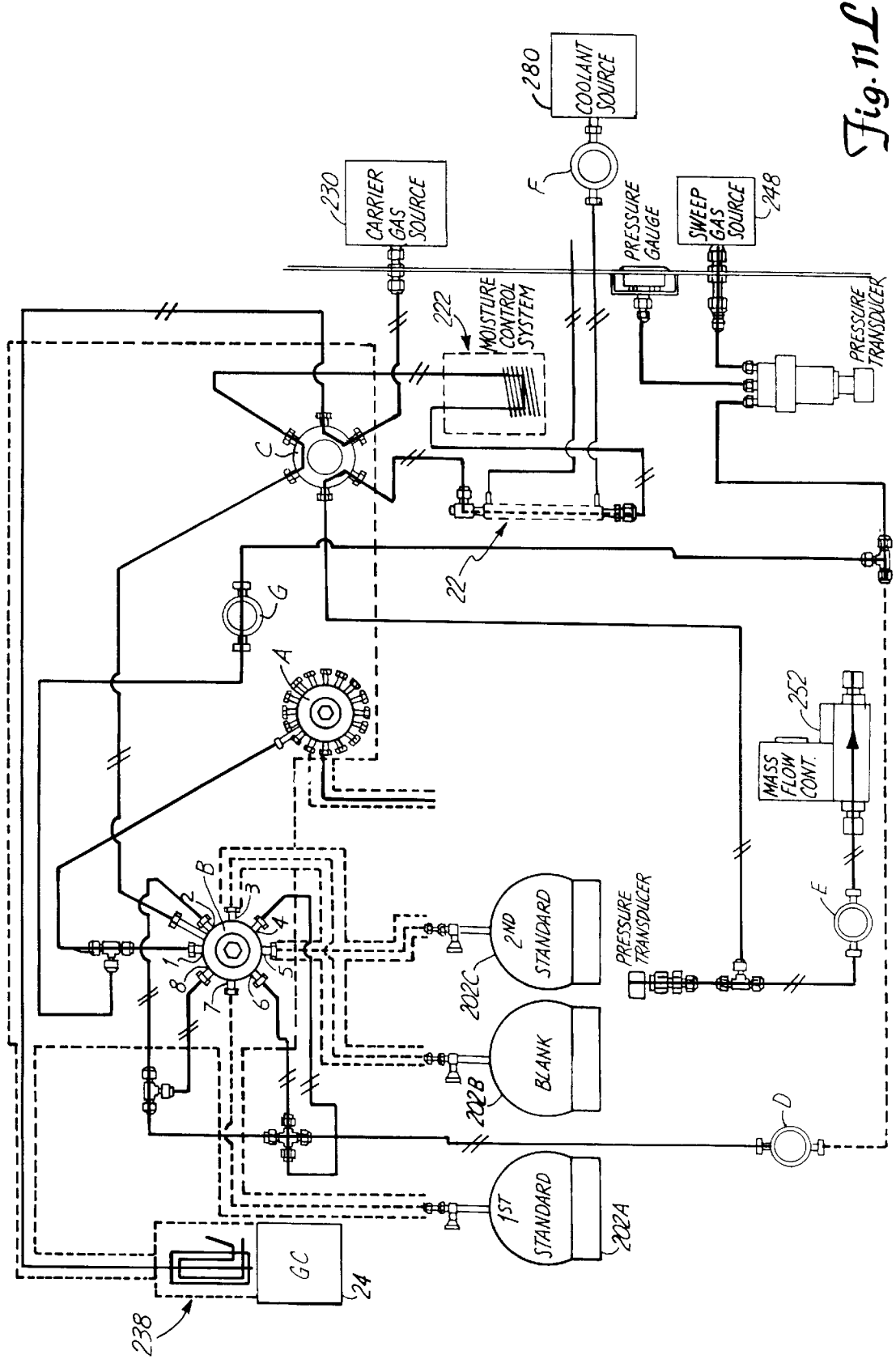
Figure 11M:
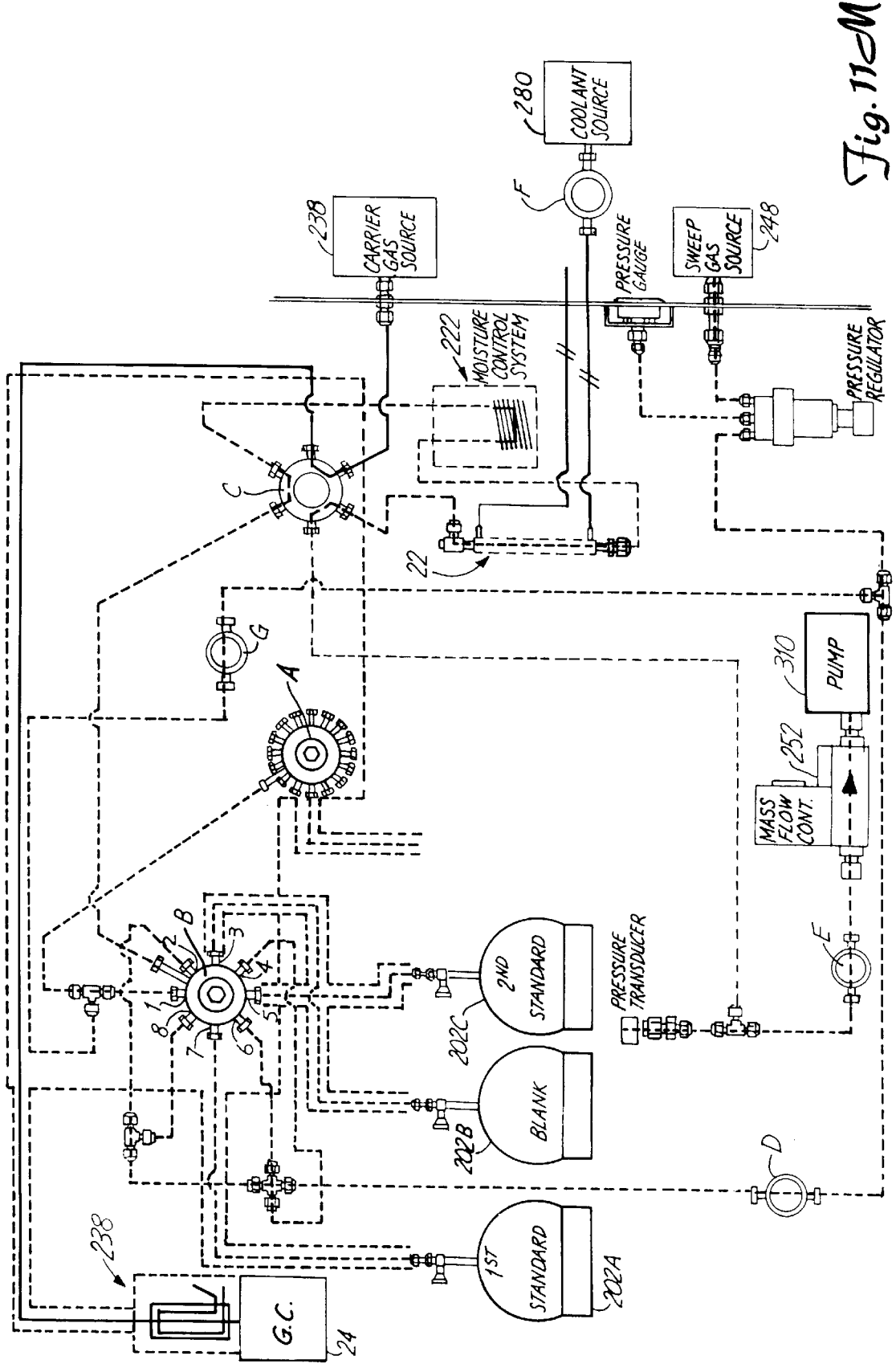
Figure 11N:
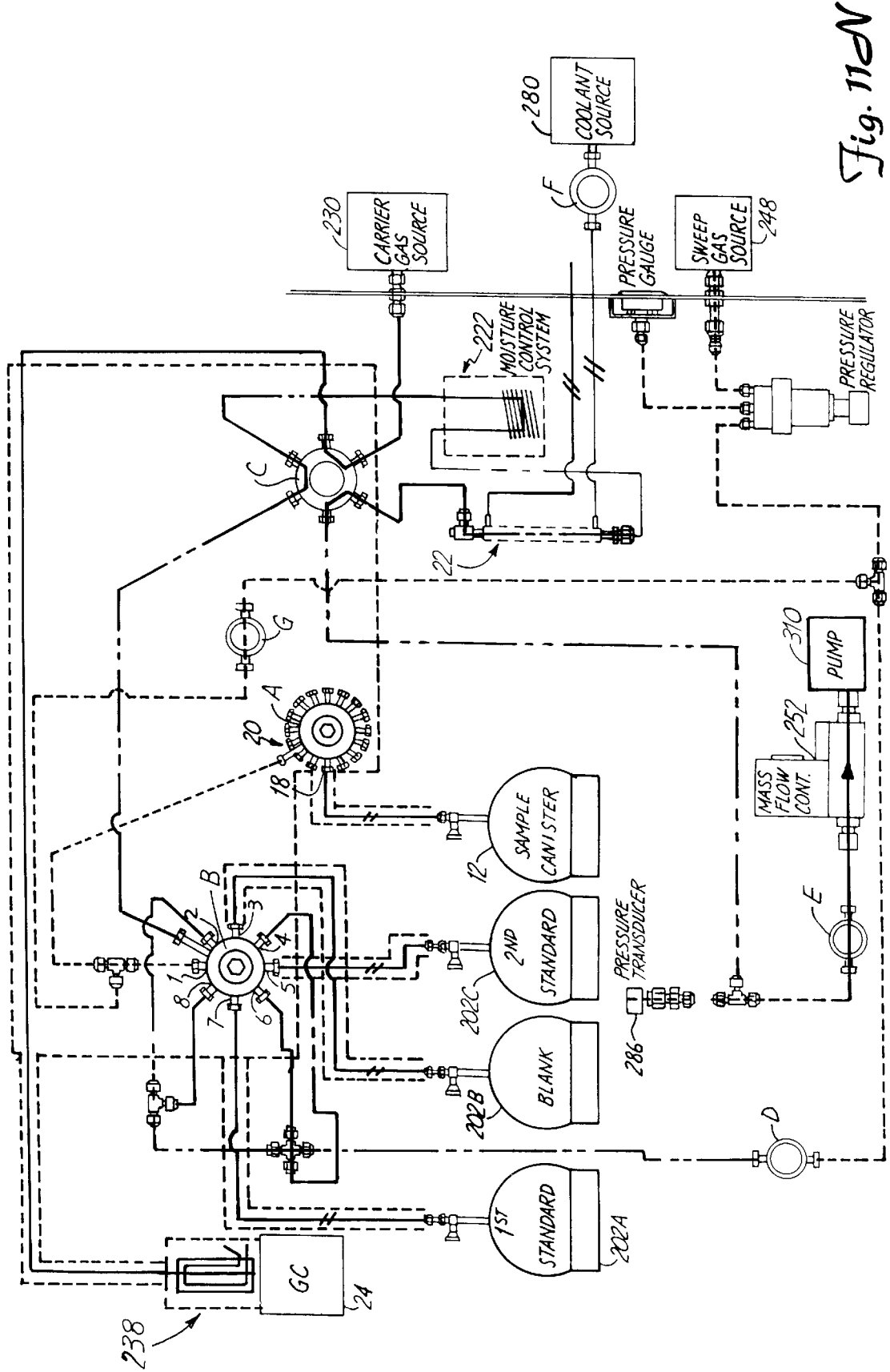

FIGS. 11A–11N illustrate various operational steps or modes of the fluid of the air system 10. In FIGS. 11A–11N, a solid line indicates gas flow through the corresponding line, a dashed line indicates that the corresponding line is pressurized and a solid line with slashes therethrough indicate no flow or significant pressure.

The various operational steps of the air sampling system 10 are also listed in Table II, below. Table II is correlated to the illustrations of FIGS. 11A–11N and indicate a state or position for valves B through G. With respect to valve B, Table II indicates a fluid coupling established between the outlet port 214 and the inlet ports 1–8. Where a listing "2, 4, 6, 8" is present, the outlet port 214 can be fluidly coupled to any of these ports. With respect to valve C, a "S" and a "D" designate the position of the valve with solid lines or dashed lines, respectively, as illustrated in FIG. 4. With respect to valves D–G, a "0" designates that the valve is off, inhibiting gas flow, and a "1" designates that the valve is on, allowing gas flow.

TABLE II

| MODE OF OPERATION | B | C | D | E | F | G |
|---|---|---|---|---|---|---|
| Standby (FIG. 11A) | 2, 4, 6, 8 | S | 1 | 1 | 0 | 0 |
| Trap Cool (FIG. 11B) | 2, 4, 6, 8 | S | 0 | 1 | 1 | 0 |
| Sample XFR (FIG. 11C) | 1 | S | 1 | 1 | 1 | 0 |
| Standard XFR (FIG. 11D) | 7 | S | 1 | 1 | 1 | 0 |
| Blank XFR (FIG. 11E) | 3 | S | 1 | 1 | 1 | 0 |
| 2nd Standard XFR (FIG. 11F) | 5 | S | 1 | 1 | 1 | 0 |
| Sweep (FIG. 11A) | 2, 4, 6, 8 | S | 1 | 1 | 0 | 0 |
| Trap Preheat (FIG. 11B) | 2, 4, 6, 8 | S | 0 | 1 | 0 | 0 |
| Drypurge (FIG. 11G) | 2, 4, 6, 8 | S | 1 | 1 | 0 | 0 |
| Trap Desorb Ready (FIG. 11H) | 2, 4, 6, 8 | S | 0 | 1 | 1 | 0 |
| Trap Desorb (FIG. 11I) | 2, 4, 6, 8 | D | 1 | 1 | 0 | 0 |
| Inject/Bake (FIG. 11J) | 2, 4, 6, 8 | S | 1 | 1 | 0 | 0 |
| Next Sample Pressure Check (FIG. 11K) | 1 | S | 1 | 1 | 0 | 0 |
| Back Flush (FIG. 11L) | 1 | S | 0 | 1 | 0 | 1 |
| Vacuum Cleaner (FIG. 11M) | 2, 4, 6, 8 | S | 1 | 1 | 0 | 0 |
| System Line Check (FIG. 11N) | 2, 4, 6, 8 | S | 0 | 1 | 0 | 1 |

FIG. 11A illustrates a "standby" mode. The system 10 is essentially idle wherein no samples are being taken from either the canisters 12 or the reference standard canisters 202A–202C. The sweep gas flows from the sweep gas source 248 through the multiposition valve B (for example, through port 8), through the multiposition valve C and the sorbent trap 22 and out through the mass flow controller 252, which controls the sweep gas flow. Neither the sorbent trap 22 or the optional trap 238 is cooled or heated in this mode. It should also be noted that in this mode and all other modes described below except for a "trap desorb" mode illustrated in FIG. 11I, the multiposition valve C is in the position indicated with solid lines in FIG. 4 so that carrier gas from the carrier gas source 230 flows to the gas chromatograph 24.

FIG. 11B illustrates a "trap cool" mode. In this mode, the valve D is turned off so as to stop the flow of sweep gas, while the valve F is turned on to allow coolant into the sorbent trap 22 to lower the temperature of the sorbent trap 22. If the sorbent trap 22 includes the GCBS material described above, the sorbent trap 22 can be cooled to approximately −100 degrees C. for a flow rate of 65 ml/min through the trap 22. This temperature is user optimizable and is dependent on flow rate. For example, at a flow rate of 35 ml/min the trap preferably is cooled to −65 degrees C.

FIG. 11C illustrates a sample being obtained from one of the canisters 12 and transferred to the sorbent trap 22. In this mode, the sorbent trap 22 is maintained at a low temperature (e.g. −100 to −65 degrees C.) by the coolant flowing from the coolant source 280. The mass flow controller 252 monitors and controls the sample gas flowing through the sorbent trap 22. When a selected quantity of gas has passed through the mass flow controller 252, the multiposition valve B can be actuated so as to fluidly couple the outlet port 214 with one of the inlet ports 2 or 8 so as to allow the sweep gas to push any remaining sample gas in the system through the trap 22. Otherwise, the multiposition valve B can be operated to access the reference standard canister 202A, if desired, before all of the sample gas has passed through the sorbent trap 22. The "sweep" mode is generally illustrated in FIG. 11A, except that coolant is allowed to flow to the sorbent trap 22 from the coolant source 280. A typical flow rate of the sample gas during the sample transfer mode is approximately 65 ml/min and may continue for 5–10 minutes.

FIG. 11D illustrates a "standard transfer" mode. In this mode, the multiposition valve B is operated so as to fluidly couple the outlet port 214 with the inlet port 7. This mode allows a selected quantity of the gas in the reference standard canister 202A to be transferred to the sorbent trap 22. The flow rates and temperatures of the sorbent trap 22 and the moisture control system 222 are similar as those described above with respect to the sample transfer mode. When a selected quantity of the reference standard 202A has been obtained as determined by the mass flow controller 252, the multiposition valve B is actuated so as to fluidly couple the outlet port 214 with the inlet port 8, if no other reference standards are to be transferred to the sorbent trap 22. If additional reference standards are to be transferred to the sorbent trap 22, the multiposition valve B can be actuated so as to fluidly couple the outlet port 214 to the inlet port 6. With either the inlet port 6 or the inlet port 8 fluidly coupled to the outlet port 214, sweep gas flows through the multiposition valve B to push any remaining reference standard in the system 10 to the sorbent trap 22.

If a second reference standard canister 202C is also to be accessed and thereby transferring a selected quantity of gas in the reference standard 202C to the sorbent trap 22, the multiposition valve B is actuated from the position where the outlet port 214 is fluidly coupled to the inlet port 6, to a position where the outlet port 214 is fluidly coupled to the inlet port 5. This mode is illustrated in FIG. 11F. In this mode, a selected quantity of gas in the second reference standard canister 202C is obtained in a manner similar to that described above in the standard transfer mode.

If the second reference standard canister 202C was accessed in the second standard transfer mode, the multiposition valve B is actuated so as to fluidly couple the outlet port 214 with the inlet port 3. The system 10 is then in a "blank transfer" mode illustrated in FIG. 11E. Utilization of a "blank" canister 202B, which contains no VOC compounds, allows the multiposition valve B to return to the sweep mode where the outlet port 214 is fluidly coupled to the inlet port 2 without reversing the multiposition valve B through ports 3–8. The multiposition valve B is then in position to fluidly couple the outlet port 214 to the inlet port 1 when the multiposition valve A is actuated to access another sample canister 12.

From the foregoing description, it should be clear that the multiposition valve B is preferably a bi-directional valve capable of fluidly connecting the inlet ports 1–8 in a clockwise or counter clockwise direction.

Where it is desirable to have three selectable reference standard canisters of known VOC concentrations, the blank standard canister 202B can be replaced with a third reference standard. The multiposition valve B can then be actuated to inject the quantities of the gases in the reference standards canisters 202A–202C. Although the reference standard canisters 202A and 202C can be selectively accessed as desired by clockwise or counter clockwise rotation of the multiposition valve B, it should be understood that the reference standard canister 202B cannot be accessed without injecting gas from one of the reference standard canisters 202A and 202C.

FIG. 11G illustrates the "drypurge" mode. In this mode, sweep gas flows through the sorbent trap 22 to remove moisture and other selected compounds such as $CO_2$. Preferably, the sorbent trap 22 is heated to an intermediate temperature sufficient to allow the $CO_2$ to be released from the sorbent trap 22 (e.g. 30 degrees C.). The sorbent trap 22 heats up quickly to its intermediate temperature (approximately 33 seconds) The valve D remains on from any previous sweep mode and through the drypurge mode.

The drypurge mode is particularly effective to remove $CO_2$ by using the GCBS-filled sorbent trap. At the intermediate temperature and low flow rate such a trap has a high retention of VOCs but readily gives up $CO_2$. Preferably, the flow rate during the drypurge mode for the sweep gas is substantially less than the sample gas flow rate during the sample transfer mode. For example, a flow rate of 3 ml/min for a duration of 3 minutes is preferred during drypurge. The flow rate, temperature and time are all adjustable in order to remove varying amounts of $CO_2$ and moisture.

FIG. 11H illustrates a "trap desorb ready" mode. In this mode, the system 10 is essentially idle wherein the controller 58 is waiting for a suitable signal from the gas chromatograph 24 indicating that any previous sample has been completely analyzed.

After the trap desorb ready mode, the system enters a "trap preheat" mode illustrated in FIG. 11B. It should be noted that when the system 10 is in the trap preheat mode, the valve F is off so as to stop the flow of coolant from the coolant source 280. During the trap preheat mode, the sorbent trap 22 is heated to a high temperature of approximately 300 degrees C.

FIG. 11I illustrates the "trap desorb" mode. In this mode, the multiposition valve C is operated to the position indicated with dashed lines in FIG. 4 so that the carrier gas from the carrier gas source 230 is fluidly coupled to the sorbent trap 22 so as to carry the VOCs collected in the sorbent trap 22 to the gas chromatograph 24. During the trap desorb mode, the sorbent trap 22 is maintained at the high temperature (approximately 300 degrees C.) to release the VOCs. If the external trap 238 is present, the VOCs collect in the trap 238, provided the trap 238 has been cooled to a sufficient temperature.

FIG. 11J illustrates an "inject/bake" mode. In this mode, the multiposition valve C has returned to the position indicated with solid lines in FIG. 4 so that the carrier gas source 230 is directly coupled to the external trap 238 or the gas chromatograph 24. If the external trap 238 is present, the external trap 238 is heated so that the concentrated VOCs collected in the external trap 238 during the desorb mode are provided to the gas chromatograph 24. Also during this mode, the sorbent trap 22 and the moisture control system 222 are heated to a sufficient temperature so that the sorbent trap 22 and the moisture control system are cleansed. During this mode, the valve D is turned on so that the sweep gas sweeps the sorbent trap 22 removing all undesired compounds.

FIGS. 11K–11N illustrate four additional modes for the system 10. FIG. 11K illustrates a "next sample pressure check" mode. In this mode, the multiposition valve A is actuated so as to fluidly connect to the next canister 12 to be sampled. The multiposition valve B is actuated so that sample gas flows through line 250 to the mass flow controller 252. After a small amount of sample gas has passed through the mass flow controller 252, valve E is shut off to pressurize the pressure transducer 286. After the pressure in the canister 12 has been checked, the valve E is opened and the multiposition valve B is actuated to one of the inlet ports 2 or 8 so that the sample gas from the canister 12 is expelled from the system 10.

Preferably, the multiposition valve A is bidirectional in that it can be advanced clockwise or counterclockwise. This feature allows canisters to be retested, or new "high priority" sample canisters to be coupled and tested, without cycling through all inlet ports of valve A. The high priority sample canister can be substituted in place of the most recently sampled canister and the multiposition valve A reversed so as to fluidly couple the high priority sample canister to the multiposition valve B.

FIG. 11L illustrates a "backflush" mode. In this mode, the valve D is turned off and the valve G is turned on. Sweep gas from the sweep gas source 248 is then allowed to backflush the multiposition valve A, and the multiposition valve A cycled through each port. Of course, the canisters 12 are disconnected from the multiposition valve A during this mode.

FIG. 11M illustrates a "vacuum clean" mode. During this mode, a vacuum pump 310 is coupled to the mass flow controller 252 to evacuate the system. Preferably, the sorbent trap 22 is heated to its bake temperature during this mode. If the valves of the canisters 12 and/or the reference standard canisters 202A–202C are closed, or the corresponding inlets are plugged, the respective inlet lines can be cleaned as well with suitable operation of the valves A and B.

FIG. 11N illustrates a "system leak check" mode. During this mode, the valve D is first closed to turn off the sweep gas. The pump 310 is operated to create a vacuum in the system from the valve D up to the valve E. The valve E is then closed and the pressure transducer 286 is monitored for any change in pressure, which would correspond to a leak in the system. During this mode, individual valves of the reference standard canisters 202A–202C and the canisters 12 are turned off.

FIG. 10 illustrates a second embodiment of an air sampling system of the present invention at 350. The air sampling system 350 includes all of the valves A–G, as described above with respect to the system 10. In addition, the air sampling system 350 includes a multiposition valve H having eight ports wherein each port is selectively fluidly connected separately to two adjacent ports. A first position is illustrated with solid lines and a second position is illustrated with dashed lines. The ports of the multiposition valve H are identified at 1, 2, 3, 4, 5, 6, 7 and 8. A small sample loop 352 (e.g. volume equals 5 microliters) is fluidly coupled to ports 3 and 6 of multiposition valve H. The multiposition valve H is controlled by the controller 58 on a signal line 354. Generally, the controller 58 operates the multiposition valve C and the multiposition valve H to capture in the sample loop 352 and any gas lines, described below, the gas from the canister 12 under test. Only this quantity of sample gas is then transferred to the sorbent trap 22 for testing. The air sampling system 350 with the multiposition valve H is particularly useful when the canister 12 under test contains high VOC concentrations, which would otherwise exceed the capabilities of the air sampling system 10 embodied in FIG. 4 or the gas chromatograph 24.

With reference to FIG. 4, the ports 1, 2, 4, 5, 7 and 8 of valve H are fluidly coupled in the gas flow lines 212, 228 and 236 of the air sampling system 10. In particular, the inlet port 1 of the multiposition valve H is fluidly coupled to the multiposition valve C with a gas line 236A. The port 2 of the multiposition valve H is coupled to the external trap 238 or the gas chromatograph 24 with a gas flow line 236B; the port 4 of the multiposition valve H is fluidly coupled to the outlet port 214 of the multiposition valve B with a gas flow line 212A; the port 5 of the multiposition valve H is fluidly coupled to the port 216 of the multiposition valve C with a gas flow line 212B; the port 7 of the multiposition valve H is fluidly coupled to the source of carrier gas 230 with a gas flow line 228A; and the port 8 of the multiposition valve H is fluidly coupled to the port 232 of the multiposition valve C with a gas flow line 228B.

When the multiposition valve H is in the position indicated with solid lines, carrier gas from the carrier gas source 230 is continuously provided to the gas chromatograph 24. Also in this position, any gas that flows from the outlet port 214 of the multiposition valve B (reference standard gases, sample gases, and sweep gas) flow through the valves H and C to the sorbent trap 22. Thus, the air sampling system 350 can operate in a manner similar to the air sampling system 10 described above when the multiposition valve H is held in the position indicated with solid lines.

The sampling of a canister having high concentrations of VOCs occurs as follows. The multiposition valve C is operated to the position indicated with dashed lines so as to isolate the sorbent trap 22 and the moisture control system 222, allowing carrier gas to flow therethrough from the carrier gas source 230. The multiposition valve B is then operated in a sample transfer mode to fluidly couple the outlet port 214 to the inlet port 1. This allows sample gas from the canister 12 under test to flow through the multiposition valve H, the sample loop 352, and the multiposition valve C (bypassing the sorbent trap 22). With a sample gas flow established, the multiposition valve B is operated to fluidly couple the sweep gas to the outlet port 214, and, simultaneously, the multiposition valve C is operated to the position with solid lines. In this manner, a known quantity of the sample gas in the sample loop 352 along with a known quantity in the lines 212A and 212B is transferred to the sorbent trap 22. It should be understood that additional known quantities of the sample gas can also be transferred to the sorbent trap 22 by cycling the multiposition valves B and C until a desired total amount (preferably integer multiples of the known amount in the sample loop 352 and lines 212A and 212B).

During the drypurge mode, the multiposition valve C remains in the position indicated with solid lines. When the sorbent trap 22 has been sufficiently heated, the multiposition valve C is operated to the position indicated with dashed lines so that carrier gas from the carrier gas source 230 flows through the sorbent trap 22, through the multiposition valve H (in the position indicated with solid lines), and carries VOCs from the sorbent trap 22 to the gas chromatograph 24.

Although the present invention has been described with reference to preferred embodiments, workers skilled in the art will recognize that changes may be made in form and detail without departing from the spirit and scope of the invention.

What is claimed is:

1. An ambient air sampler for obtaining air samples from sample enclosures and concentrating constituents contained in the air samples, the ambient air sampler comprising:
    a stand adapted to support the sample enclosures at spaced-apart locations;
    a multiposition valve carried by the stand, the multiposition valve having a plurality of inlet ports and an outlet port selectively fluidly coupleable to any of the plurality of inlet ports;
    a plurality of inlet lines, wherein each inlet line has a first end fluidly coupled to one of the inlet ports and a second end fluidly coupleable to one of the sample enclosures;
    a concentrator trap carried by the stand and fluidly coupleable to the outlet port to concentrate the constituents from at least one of the air samples; and
    a heating device for heating at least a portion of each of the inlet lines, the heating device having a slot extending inwardly to a cavity, wherein said at least a portion of each of the inlet lines is disposed in the cavity with the corresponding inlet lines extending through the slot at spaced-apart locations.

2. The ambient air sampler of claim 1 wherein the heating device comprises a heatable surface.

3. The ambient air sampler of claim 2 wherein the heating device comprises a heating element thermally coupled to the heatable surface.

4. The ambient air sampler of claim 3 wherein the heating device comprises an insulator insulating the heatable surface.

5. The ambient air sampler of claim 1 wherein the trap includes a sorbent bed consisting essentially of a single compound.

6. The ambient air sampler of claim 5 wherein the single compound is a graphitized carbon based sorbent.

7. The ambient air sampler of claim 1 wherein the trap includes an injection port for injecting a known sample therein.

8. An ambient air sampler, comprising:
    a stand adapted to support a plurality of sample enclosures at spaced-apart locations;
    a multiposition valve mounted to the stand, the multiposition valve having an outlet port and a plurality of inlet ports selectively fluidly coupleable to the outlet port;
    a plurality of inlet lines wherein each inlet line has a first end fluidly coupled to one of the inlet ports and a second end fluidly coupleable to one of the sample enclosures;
    a concentrator trap carried by the stand and coupleable to the outlet port to concentrate selected constituents from the sample enclosure, the trap including an injection port for injecting a known sample through a self-sealing septum.

9. The ambient air sampler of claim 8 wherein the trap is mounted to the stand and the injection port extends through an outer surface of the stand.

10. The ambient air sampler of claim 8 and further comprising a manifold having a plurality of spacedapart apertures, wherein an inlet line extends through each of the spaced-apart apertures.

11. The ambient air sampler of claim 10 and further comprising a heating device to heat the manifold.

12. The ambient air sampler of claim 8 wherein the trap includes a trap tube and an enclosure surrounding the trap tube forming a chamber therebetween for the circulation of a fluid to cool the trap tube.

13. The ambient air sampler of claim 12 wherein the enclosure includes a first port opening to the chamber and a second port opening to the chamber, the first port and the second port being fluidly connectable to a source of cooling fluid.

* * * * *

UNITED STATES PATENT AND TRADEMARK OFFICE
CERTIFICATE OF CORRECTION

PATENT NO.   : 5,847,291
DATED        : December 8, 1998
INVENTOR(S)  : Green et al.

It is certified that error appears in the above-identified patent and that said Letters Patent is hereby corrected as shown below:

Page 1 of 1

Column 14, line 28, replace "spacedapart" with
--spaced-apart--.

Signed and Sealed this

Thirtieth Day of March, 1999

Attest:

Q. TODD DICKINSON

*Attesting Officer*            *Acting Commissioner of Patents and Trademarks*